United States Patent
Son et al.

(10) Patent No.: US 11,470,944 B2
(45) Date of Patent: Oct. 18, 2022

(54) ELASTIC MICROCELL SURFACE STRUCTURE AND METHOD FOR MANUFACTURING SAME

(71) Applicants: Kwang Oh Son, Seoul (KR); Sang Yeoul Son, Seoul (KR)

(72) Inventors: Kwang Oh Son, Seoul (KR); Sang Yeoul Son, Seoul (KR); Ral Ra Lee, Seoul (KR); Ki Hyung Ma, Yongin-si (KR)

(73) Assignees: Kwang Oh Son, Seoul (KR); Sang Yeoul Son, Seoul (KR)

( * ) Notice: Subject to any disclaimer, the term of this patent is extended or adjusted under 35 U.S.C. 154(b) by 372 days.

(21) Appl. No.: 16/764,576

(22) PCT Filed: Nov. 7, 2018

(86) PCT No.: PCT/KR2018/013427
§ 371 (c)(1),
(2) Date: May 15, 2020

(87) PCT Pub. No.: WO2019/098591
PCT Pub. Date: May 23, 2019

(65) Prior Publication Data
US 2021/0169200 A1    Jun. 10, 2021

(30) Foreign Application Priority Data

Nov. 16, 2017  (KR) .......................... 10-2017-0153035
Feb. 16, 2018  (KR) .......................... 10-2018-0018862
Nov. 6, 2018   (KR) .......................... 10-2018-0134960

(51) Int. Cl.
A45D 34/04    (2006.01)
A45D 33/34    (2006.01)
(Continued)

(52) U.S. Cl.
CPC ................ *A45D 34/04* (2013.01); *A61K 8/87* (2013.01); *A45D 33/34* (2013.01);
(Continued)

(58) Field of Classification Search
CPC .. A45D 34/04; A45D 33/34; A45D 2033/001; A45D 2034/002;
(Continued)

(56) References Cited

U.S. PATENT DOCUMENTS

2002/0039513 A1* 4/2002 Pink ..................... A45D 34/045
                                                        401/129
2003/0077440 A1* 4/2003 Razavi .................... B32B 15/08
                                                        428/354
2013/0248089 A1* 9/2013 Su ........................... B25G 1/10
                                                        156/192

FOREIGN PATENT DOCUMENTS

JP    2003-531742 A    10/2003
JP    2005-177163 A     7/2005
(Continued)

OTHER PUBLICATIONS

Search Report, dated Feb. 28, 2019, for International Application No. PCT/KR2018/013427.
(Continued)

*Primary Examiner* — David J Walczak
(74) *Attorney, Agent, or Firm* — LRK Patent Law Firm

(57) ABSTRACT

An elastic microcell surface structure for an elastomer body with an outer film adhered and to a method for manufacturing the same, wherein the elastomer body includes a solid uneven structure formed of protruding portions and recess portions formed in its surface, and the outer film includes a zigzag uneven structure in a manner of being tightly wrapped around the protruding portions and recess portions of the solid uneven structure of the elastomer body.

18 Claims, 25 Drawing Sheets

(51) Int. Cl.
    *A45D 33/00*     (2006.01)
    *A45D 34/00*     (2006.01)
    *A45D 40/00*     (2006.01)
    *A61K 8/87*     (2006.01)
    *B29C 33/42*     (2006.01)

(52) U.S. Cl.
    CPC .. *A45D 2033/001* (2013.01); *A45D 2034/002* (2013.01); *A45D 2040/0006* (2013.01); *B29C 33/424* (2013.01)

(58) Field of Classification Search
    CPC .. A45D 2040/0006; A61K 8/87; B29C 33/38; B29C 33/424; B29C 70/44; B29C 59/02; B65H 81/06
    USPC .......................... 132/200; 401/261, 264, 266
    See application file for complete search history.

(56) References Cited

FOREIGN PATENT DOCUMENTS

| | | |
|---|---|---|
| JP | 2009-201833 A | 9/2009 |
| KR | 20-0472813 Y1 | 5/2014 |
| KR | 10-1523518 B1 | 5/2015 |
| KR | 10-2015-0071599 A | 6/2015 |
| KR | 10-1733418 B1 | 5/2017 |
| KR | 10-1743610 B1 | 6/2017 |
| KR | 10-2017-0094098 A | 8/2017 |
| KR | 10-1795372 B1 | 11/2017 |

OTHER PUBLICATIONS

Written Opinion, dated Feb. 28, 2019, for International Application No. PCT/KR2018/013427.

\* cited by examiner

1100

ELASTIC MICROCELL SURFACE STRUCTURE AND METHOD FOR MANUFACTURING SAME

CROSS-REFERENCE TO RELATED APPLICATIONS

The present application is a U.S. National Phase entry from International Application No. PCT/KR2018/013427, filed Nov. 7, 2018, which claims priority to Korean Patent Application Nos. 10-2017-0153035, filed Nov. 16, 2017, 10-2018-0018862, filed Feb. 16, 2018, and 10-2018-0134960, filed Nov. 6, 2018, the disclosures of which are incorporated by reference herein in their entirety.

BACKGROUND

1. Technical Field

The present disclosure relates to an elastic microcell surface structure and a method for manufacturing the same, which relates to a surface structure in which an outer film of a thin film such as a thermoplastic polyurethane is tightly adhered to a low-hardness, high-elasticity resin elastomer such as silicone rubber. That is, a surface of the solid uneven structure (irregularities) formed on the surface of the elastomer body is tightly adhered to the outer film so that the elastomer body and the outer film together form a fine emboss surface. For example, when the solid uneven structure is applied to the dispensing surface of the cosmetic applicator or to the surface of the mouse pad, there is no surface slip phenomenon and the tactile feeling can be improved.

2. Description of Related Art

In general, cosmetic applicators, also referred to as cosmetic puffs, are widely known as cosmetic tools to a user by taking a cream type or liquid type cosmetic and applying it to skin such as a face. Conventional cosmetic puffs are mostly manufactured using a sponge with a large number of pores. Although the existing sponge-made cosmetic puff has an advantage of high adsorption, it has a disadvantage that cosmetic residual substances are not easily removed by being penetrated into the pores inside the sponge. The cosmetic residues left on the sponge puff are not good for hygiene because it easily became a bacterial habitat.

Therefore, the user feels an inconvenience of periodically washing the cosmetic puff or being exposed to the risk of bacterial contamination by continuous use of the cosmetic puff, or discarding the cosmetic puff used for a certain period of time and replacing it with a new one. Furthermore, the existing sponge-made cosmetic puff has a large amount of cosmetics remaining in the puff itself. As a result, there was a problem that this expensive cosmetic product was wasted.

In order to solve such problems of the sponge puff, a silicone puff using an elastomer body made of a material such as silicone rubber has recently been proposed. The silicone puff is composed of an elastomer body made of silicone rubber as a main substance and a thin outer shell made of a material such as polyurethane. Silicone rubber is closely contacted to the skin or has a softer, low hardness, providing the advantage of good tactile feeling. And since there are no cosmetic residues absorbed into the silicone puff, cosmetics are saved. In addition, the cosmetic residue on the surface of the silicone puff can be easily removed through a means such as a wet wipe, so it can be used hygienically. Furthermore, the silicone puff provides various advantages such as a long life period compared with a sponge due to its high durability.

However, since the surface of the conventional silicone puff is smooth, there is a disadvantage that an appropriate amount of cosmetics cannot be accommodated in the surface of the puff during makeup. In addition, there is a problem that the gel or liquid cosmetic product slides between the silicone puff surface and the skin slides to reduce the friction between the puff surface and the skin surface. For this reason, it is not easy for the user to apply the desired amount of cosmetics to the desired skin location, which is inconvenient, and there is a problem that the tactile feeling to the skin is not good. Furthermore, in the case of makeup on a rough skin surface with many skin pores, there is also a problem that the cosmetic on the puff surface is not easily applied to the uneven portion between the skin pores.

Therefore, there is a need for a technique capable of reducing friction between the surface of the silicon puff and the skin. To meet this, various ideas have been proposed to form wrinkles or emboss on the surface of a silicon puff. For example, Japanese Patent Application Laid-open Publication No. 2005-177163 discloses a cosmetic puff having a gel material wrapped with a stretchable film being embossed on the surface. This technology is intended to provide irregularities on the surface of a silicone puff by forming emboss on the outer film made of a polyurethane material, rather than an elastomer body made of a silicone rubber material. However, the outer film formed with the emboss pattern has a problem of poor adhesion to a silicone rubber elastomer body. In addition, there is a technical limitation that the thinner the outer film is, the more difficult it is to form the emboss pattern in a desired size.

In other words, a polyurethane film having a thickness of approximately 30 to 120 μm is used as the stretchable film forming the outer skin of the cosmetic puff in the prior art. If the emboss is formed on the polyurethane film itself, the thickness of the uneven portion of the emboss has a smaller value than the thickness of the outer film, and therefore, it is inevitably smaller than 120 μm in thickness. It is obvious that the cosmetics cannot be effectively applied to the skin using the emboss structure having a recess portion of such a thin depth. If the emboss is formed by bending the outer film in a zigzag manner, that is, when a zigzag emboss structure is formed, the contact area between the film having the zigzag emboss structure and the inner member becomes small, resulting in poor adhesion. Therefore, in this case, a separate adhesive layer should be added to maintain the adhesive force between the zigzag emboss film and the inner member.

In general, the thinner the thickness of the polyurethane film forming the outer surface of the silicone puff, the more preferable is that it does not interfere with the soft tactile feeling of the silicone rubber disposed inside. It is common to use a thin film having a thickness of about 0.01 to 0.05 mm with a polyurethane film for an outer skin in a cosmetic silicone puff currently being made. This has the advantage that it is usually manufactured in a roller compaction method, having a uniform thickness, high elasticity and high durability. However, in practice, it is not easy to emboss the surface of the thin polyurethane film. In order to emboss, the polyurethane film must be compressed with a roller having a surface on which an emboss structure is formed. At this case, if the temperature of the roller is high, the film is easily torn, and if the temperature is low, the emboss is not easily formed on the film due to its high elasticity. Even if the thin polyurethane film is emboss processed, a separate adhesive layer is additionally needed to maintain adhesion force at the boundary area between the emboss polyurethane film and the silicone rubber, to make the outer skin into two layers, which deteriorates tactile feeling. In addition, since the thickness of the polyurethane film itself is thin, the size of the emboss structure formed on the surface becomes also very small, so that it is not suitable for use for cosmetic application.

As another example, Korean Patent Registration No. 10-1733418 describes a cosmetic puff. In the process of manufacturing the cosmetic puff, a heat-fusion mold having an emboss forming portion is prepared, and the upper and lower surface sheets and silicone gel pads are disposed in the mold. Then, by applying pressure and heat, an emboss pattern is formed on the puff surface. This idea includes that the mold has the emboss forming portion, and that the emboss pattern on the surface of a silicon puff is formed by pressure and heat-sealing.

In general, the surface sheet of the silicone puff uses a thermoplastic resin, so it can be deformed by heat. However, the silicone rubber disposed inside of the silicone puff is two-compound type or thermosetting type, and once cured, the shape is not deformed by heat. Therefore, the cured silicone material such as a silicone gel pad, is not deformed by heat. Therefore, according to this idea, the emboss pattern is formed only on the surface sheets surrounding the silicone gel pad. The depth of the emboss pattern formed on the thin surface sheet is inevitably formed in a depth smaller than the thickness of the surface sheet. So, there is still a problem that a shallow depth emboss formed on the surface sheet is not suitable for applying a liquid or creamy cosmetic product to the skin.

As another example, Japanese Patent Application Laid-open Publication No. 2009-201833 describes a cosmetic puff. In this case, a thin urethane surface film is formed by spray coating the urethane solution on a mold having an emboss pattern and then rotating the mold. Then, liquid silicone or urethane is injected and cured, and as a result, the emboss pattern is formed on the surface. In this case, the urethane surface film forming the surface of the silicon puff is cured after being sprayed. Compared to the polyurethane film produced by the conventional roller compression method, the surface film formed by spraying is difficult to secure the uniformity of the thickness. Additionally, since the surface film is not compressed, the elasticity is poor and the durability is not high. Therefore, there is still a problem that the tactile feeling is not good and it is difficult to provide a practical cosmetic applicator.

SUMMARY OF THE INVENTION

The inventor has been looking for a technique for forming emboss in a surface structure For example, the surface structure of an applicator such as a cosmetic silicone puff for applying a gel or liquid material is the surface structure with two elements of different materials, which are in close contact with each other, for example, a polyurethane outer film and a silicone rubber elastomer. The inventor has realized that although the silicone rubber material is difficult to mold in a cured state, it can be molded by adapting the silicone rubber material to the shape of the mold in the liquid form before curing; that therefore, if the liquid silicone rubber is adhered to the mold emboss surface and then molded, an emboss structure can be formed on the silicone rubber surface; and that however, in order to adhere the liquid silicone rubber to the mold emboss surface, the polyurethane outer film surrounding the outside of the silicone rubber must first be brought into close contact with the mold emboss surface.

Furthermore, the inventor has realized that in order to adhere the thin outer film to the mold emboss surface, it is necessary to completely remove the air between the mold emboss surface and the outer film and to pressurize the mold at the same time; that to this end, when forming a vent hole for removing air in the mold, it needs to form the vent hole to the extent that the durability of the mold is not impaired; that if the side portion of each recess is a well shape surrounded by a protrusion, the vent hole must be formed for each and every recesses, and as a result, the mold manufacturing cost is increased and the mold durability is lowered. Therefore, it is necessary that among the protrusions and recesses constituting the mold emboss surface, each recess portion is not formed into an isolated well structure, instead formed in the form of an isolated island, resulting, air can move through the side portion of each recess toward the adjacent recesses. In this case, air in the recesses communicating with each other in the lateral direction can be effectively removed by forcibly sucking the air in the lateral direction.

In addition, the present inventor has realized that a surface structure in which the thin outer film is in close contact with the silicone rubber can be applied as a dispensing surface of a cosmetic applicator. In addition, the surface structure can be applied to various products in which the surface serves an important function, such as a mouse pad. In this case, compared to a product having a smooth surface, it is possible to provide a useful effect in which there is no surface slip phenomenon and the tactile feeling is improved.

The present disclosure has an object to provide an elastic microcell surface structure in a form in which an outer film such as a thin thermoplastic polyurethane is in close contact with an elastomer body made of a low-hardness and high-elasticity resin such as silicone rubber. The surface structure forms an emboss pattern having protrusions on the surface of the elastomer body and recesses surrounded by the protrusions. The outer film is configured to be in close contact along all of the surfaces of the emboss pattern of the elastomer body, and accordingly, it is possible to provide the emboss structure having desired depths, for example, as the depths of the recesses may be 2 to 20 times the thickness of the outer film.

Furthermore, an object of the present disclosure is to provide an elastic microcell surface structure in a form in which an outer film such as a thin thermoplastic polyurethane is in close contact with an elastomer body made of a low-hardness and high-elasticity resin such as silicone rubber. In the surface structure an emboss pattern is formed on the surface of the elastomer body having continuous protrusions in the form of a mesh and a plurality of micro cell recesses separated by the protrusions. The outer film is in close contact with the protrusions and recesses of the emboss pattern of the elastomer body, and accordingly, an emboss pattern can be easily produced.

Furthermore, an object of the present disclosure is to provide an elastic microcell surface structure in a form in which an outer film such as a thin thermoplastic polyurethane is in close contact with an elastomer body made of a low-hardness and high-elasticity resin such as silicone rubber. On the surface of the elastomer body, an emboss pattern having a plurality of microcell recesses of various widths, which are continuous in the form of a mesh and have various widths and is separated by the projections, is formed. The outer film is configured to be in close contact with the protrusions and recesses of the emboss pattern on the surface of the elastomer body. Accordingly, it is possible to form various types of emboss patterns that are functionally diverse and can satisfy various aesthetic needs of consumers.

In addition, an object of the present disclosure is to provide a method for manufacturing elastic microcell surface structure in which an outer film such as a thin thermoplastic polyurethane is in close contact with an elastomer body made of a low-hardness and high-elasticity resin such as silicone rubber. The method comprises preparing a mold cavity having an emboss pattern having a plurality of recesses and a plurality of protrusions isolated by the continuous recesses; disposing an outer film on the surface of the mold cavity emboss pattern; removing air between the emboss pattern surface of the mold cavity and the outer film to adhere the outer film to the emboss pattern surface; injecting a liquid elastomer composition into the mold-film double layer with the emboss structure formed by adhering the outer film to the emboss pattern surface of the mold cavity; and curing the liquid elastomer composition. Accordingly, an emboss pattern corresponding to the mold-film double layer with the emboss structure is formed on the surface of the elastomer body, and then the outer film is in close contact along all of the surfaces of the protrusions and recesses of the formed elastic emboss pattern. For example, the depth of the emboss recesses of the elastomer body may be 2 to 20 times the thickness of the outer film, and it is possible to provide an elastic microcell surface structure having recesses of desired depth.

Furthermore, an object of the present disclosure is to provide a method, in which the mold cavity emboss pattern includes continuous recesses in the form of a mesh and a plurality of protrusions separated by the recesses, and the outer film is in close contact with the surfaces of the continuous recesses and the isolated protrusions of the mold cavity emboss pattern. The mold-film double-layer with emboss structures includes continuous recesses and a plurality of protrusions separated by the recesses in the same manner as the mold cavity emboss pattern. The emboss pattern on the surface of the elastomer body formed correspondingly includes continuous protrusions in the form of a mesh and a plurality of recesses separated by the protrusions, and accordingly, the air between the outer film and the mold cavity emboss pattern may be easily sucked through the continuous recesses.

Furthermore, an object of the present disclosure is to provide a method, in which the mold cavity emboss pattern includes continuous recesses with various widths in a mesh shape and a plurality of protrusions having various widths separated by the recesses. The outer film is in close contact with the surfaces of the continuous recesses and the isolated protrusions of the mold cavity emboss pattern. Accordingly, the mold-film double-layer with emboss structures includes recesses having various widths continuous in a mesh shape and a plurality of protrusions of various widths separated by the recesses in the same manner as the mold cavity emboss pattern. In addition, the emboss pattern formed on the surface of the elastomer body is formed correspondingly to have a plurality of recesses with various widths separated by protrusions of various widths continuous in a mesh shape, and accordingly, various types of emboss patterns can be formed on the that are functionally diverse and can satisfy various aesthetic needs of consumers.

The present disclosure is to provide an apparatus for manufacturing elastic microcell surface structure that can be used as an applicator coating surface in the form of an elastomer body made of a low-hardness, high-elasticity resin such as silicone rubber wrapped with an outer film such as a thin thermoplastic polyurethane. The manufacturing apparatus includes: a mold cavity having an emboss pattern having continuous recesses in a mesh shape and a plurality of protrusions isolated by the recesses; a heater for heating the mold cavity to a predetermined temperature; a pressing member for sealing the space between the mold cavity emboss pattern surface and the outer film by pressing the edge of the outer film disposed on the mold cavity emboss pattern surface along the edge of the mold cavity; a suction pump for sucking and removing air in the space between the mold cavity emboss pattern surface and the outer film so that the air between the mold cavity emboss pattern surface and the outer film is removed to adhere the outer film to the emboss pattern surface. Then, a liquid elastomer composition is injected and cured on the mold-film double-layer emboss structure formed by adhering the outer film to the emboss pattern surface of the mold cavity, accordingly, an emboss pattern corresponding to the mold-film double layer emboss structure is formed on the surface of the elastomer body. The outer film is in close contact with the convex and concave surfaces of the elastic emboss pattern being formed, accordingly, and the manufacturing apparatus can manufacture a microcell elastic surface structure having a recess portion of a desired depth. For example, the depth of the embossed recess portion of the elastomer body may be 2 to 20 times the thickness of the outer film.

Furthermore, an object of the present disclosure is to provide an apparatus, in which the mold cavity emboss pattern includes continuous recesses in the form of a mesh and a plurality of protrusions separated by the recesses, and the outer film is in close contact with the surfaces of the continuous recesses and the isolated protrusions of the mold cavity emboss pattern. The mold-film double layer emboss structure includes continuous recesses in a mesh shape and a plurality of protrusions separated by the recess portion in the same manner as the mold cavity emboss pattern. The emboss pattern formed on the surface of the elastomer body corresponding to the mold-film double-layer emboss structure includes continuous protrusions in the form of a mesh and a plurality of recesses separated by the protrusions, accordingly, the apparatus may be configured to easily remove air between the outer film and the mold cavity emboss pattern through the continuous recesses.

Furthermore, an object of the present disclosure is to provide an apparatus, in which the mold cavity emboss pattern is made of a separate emboss pattern member and is assembled to the manufacturing apparatus, accordingly, it is easy to remove the air between the outer film and the mold cavity emboss pattern through the gap located along the edge of the emboss pattern member connected to the continuous recess, and the mold cavity emboss pattern can also be easily changed to a desired pattern.

Furthermore, an object of the present disclosure is to provide an apparatus. The mold cavity emboss pattern includes recesses of various widths continuous in a mesh shape and a plurality of protrusions of various widths separated by the recesses, and the outer film is in close contact with the surfaces of the continuous recesses and the isolation protrusions of the mold cavity emboss pattern, accordingly, the mold-film double-layer embossing structure includes a plurality of recesses of various widths continuous in a mesh shape and a plurality of protrusions of various widths separated by the recesses, similar to the mold cavity emboss pattern. The emboss pattern formed on the surface of the elastomer body, which is formed correspondingly to the mold-film double-layer embossing structure, includes a plurality of recesses with various widths separated by protrusions having various widths, continuously formed in a mesh shape, accordingly, various types of emboss patterns can be formed that are not only functionally diverse but also satisfies various aesthetic needs of consumers.

Above objects are achieved by elastic microcell surface structure, method for manufacturing thereof, and apparatus for manufacturing thereof according to the present disclosure.

According to one aspect of the present disclosure, there is provided an elastic microcell surface structure for an elastomer body with an outer film adhered, and the outer film is tightly adhered on the surface of the emboss pattern having protruding portions and recess portions of the elastomer body.

According to an exemplary embodiment, in the solid uneven structure (irregularities) of the elastomer body, the protruding portions may be connected to each other in a horizontal direction in the form of a net and are continuous, and the recess portions may include a plurality of recesses in which each of the recesses is isolated by the protruding portions continuously connected in the form of a net.

According to an exemplary embodiment, the thickness of the outer film may be 0.01~0.10 mm, and the depth of the recess portions may be 2 to 20 times the thickness of the outer film.

According to an exemplary embodiment, the elastomer body may comprise silicone rubber or urethane rubber.

According to an exemplary embodiment, the envelope film may comprise a thermoplastic polyurethane film.

According to another aspect of the present disclosure, there is provided a method of manufacturing an elastic microcell surface structure for an elastomer body with an outer film adhered, comprising: preparing a mold cavity having an emboss pattern of solid uneven structure having continuous recess and protruding portions surrounded by the continuous recesses; disposing an outer film over the surface of the emboss pattern of the mold cavity; removing air between the surface of the emboss pattern of the mold cavity and the outer film so that the outer film may closely adhere onto the surfaces of the recess portions and the protruding portions of the emboss pattern of the mold cavity; introducing a liquid composition into the mold-film double layer emboss structure formed by tightly adhering the outer film on the surface of the emboss pattern of the mold cavity; and curing the liquid composition.

According to an exemplary embodiment, the recess portion of the emboss pattern may be a recess that is formed by connecting the recess portions laterally in the form of a mesh, the protruding portions of the emboss pattern may include a plurality of protrusions separated by the recesses, and air between the outer film and the surface of the emboss pattern may be removed through the recess portions connected to each other in the form of the net.

According to an exemplary embodiment, after curing the liquid elastomer composition, the method may further comprise: separating a semi-finished product from the mold cavity, in which the semi-finished product has the cured elastomer body and the outer film tightly adhered thereon; and arranging a cover film and a ribbon holder strip on the separated semi-finished product; and thermally bonding and cutting the outer film, the cover film and the ribbon holder strip along the edge of the semi-finished product.

According to an exemplary embodiment, after curing the liquid composition, the method may further comprise: separating a pair of semi-finished products from the mold cavity, in which each of the semi-finished products has the cured elastomer body and the outer film tightly adhered thereon; overlapping the pair of separated semi-finished products such that the top surfaces of the elastic bodies are in contact with each other; and thermally bonding and cutting the outer films of the pair of the semi-finished products along the edge thereof.

According to an exemplary embodiment, after curing the liquid elastomer composition, the method may further comprise: separating a semi-finished product from the mold cavity, in which the semi-finished product has the cured elastomer body and the outer film tightly adhered thereon; covering a cover film on top of the separated pair of semi-elastomer body, respectively; overlapping the pair of semi-finished products covered with the cover film such that the two cover films are in contact with each other; arranging a protective film between two overlapping cover films to cover only a part of an edge of the semi-finished product; and thermally bonding and cutting the outer film and the cover film along the edge of the semi-finished product.

According to yet another aspect of the present disclosure, there is provided an apparatus for manufacturing an elastic microcell surface structure for an elastomer body with an outer film adhered, comprising: a mold cavity having an emboss pattern comprised by continuous recess portions and protruding portions surrounded by the continuous recess portions; a heater for heating the mold cavity to a predetermined temperature; a pressing member for sealing the space between the surface of the emboss pattern of the mold cavity and an outer film disposed thereon by pressing the edge of the outer film along the edge of the mold cavity; and a suction pump for sucking and removing air from the space between the surface of the emboss pattern and the outer film.

According to an exemplary embodiment, the recess portions of the emboss pattern may be connected laterally to each other in a net form, and the protruding portions of the emboss pattern may include a plurality of protrusions isolated by the recess portions.

According to an exemplary embodiment, the emboss pattern of the mold cavity may be formed by a separately manufactured pattern member, and the pattern member is assembled inside the mold cavity.

And, according to the present disclosure, there are provided a cosmetic applicator comprising a dispensing surface provided with the elastic microcell surface structure described above, and a mouse pad comprising a contact surface which may contact a mouse or a user wrist, in which the contact surface comprises the elastic microcell surface structure described above.

Advantageous Effects

According to the present disclosure, there may be provided an elastic microcell surface structure that can be used, for example, as a dispensing surface of a cosmetic applicator or a mouse/wrist contact surface of a mouse pad. For example, there may be provided an elastic microcell surface structure in which an outer film such as a thermoplastic polyurethane having a thickness of, for example, 0.01 to 0.10 mm is adhered to an elastic surface of a low hardness silicone rubber having a shore hardness of 10 to 45, for example. In particular, according to the present disclosure, the outer film is closely adhered to the surface of the mold cavity having the emboss pattern, and as a result, the mold and the outer film are formed together to form a mold-film double layer emboss structure. And then, by introducing a liquid elastomer composition such as a liquid silicone rubber into the mold-film double layer emboss structure thus formed, the liquid elastomer may form a shape corresponding to the mold-film double layer emboss pattern. In this state, when a predetermined time elapses, the liquid elastomer composition may be cured, so that an emboss pattern corresponding to the mold-film double layer emboss structure may be formed on the surface of the elastomer body.

In such an elastic microcell surface structure provided by the present disclosure, an emboss pattern is formed on both the outer film and the elastomer body. Here, the emboss structure formed on the elastomer body is an uneven structure (irregularities) in which a plurality of concave and convex portions are formed on the surface of the elastomer body. On the other hand, the emboss structure formed on the outer film is an uneven structure that forms a zigzag pattern created by alternating bending in which the film itself is bent and waved. In descriptions of the present disclosure, in order to clearly distinguish the emboss structure of the elastomer body from that of the outer film, the emboss structure of the elastomer body is referred to as a "solid uneven structure" and the emboss structure of the outer film is referred to as a "zigzag uneven structure".

In other words, the structure of the emboss pattern formed on the elastic microcell surface structure according to the present disclosure is characterized by having a solid uneven structure in which recesses and protrusions are formed on the surface of the elastomer body. Furthermore, the outer film in close contact with the elastomer body does not have an uneven structure in itself, but is deformed to have a zigzag pattern by adhering along the surface of the solid uneven structure of the elastomer body. Accordingly, the outer film has a characteristic of forming a zigzag uneven structure formed along the surface of the solid uneven structure of the elastomer body.

In the elastic microcell surface structure of the provided by the present disclosure, it is preferable that the depth of the recess is at least two times greater than the thickness of the outer film. For example, the depth of the recess may have a depth of 2 to 20 times the thickness of the outer film. In a preferred exemplary embodiment, the depth of the recess is 8 to 15 times the thickness of the outer film. On the other hand, in the emboss pattern formed on the elastic microcell surface structure, the width of the recess is not limited if the condition that the outer film has to be at least 4 times larger than the thickness of the outer film is satisfied because the outer film must be in close contact with all of the side walls of the recess. In addition, the distance between the recesses (that is, the width of the protrusions) may be constant or may have various sizes according to a pattern of a desired shape, and is not limited.

In addition, according to the present disclosure, unique features are provided. During the manufacturing process, the outer film is closely contacted to the embossing structure of the mold to form a "mold-film double layer emboss structure". Then, a solid uneven structure of the elastomer body is formed by introducing and curing a liquid elastomer composition (for example, silicone rubber liquid) into the mold-film double layer emboss structure.

In such a mold-film double layer emboss structure, the emboss structure of the mold forms a solid uneven structure in the form of recesses and protrusions formed on the surface of the mold. On the other hand, the outer film is in close contact with the recesses and protruding surfaces of the solid uneven structure of the mold, thereby forming a zigzag uneven structure formed along the surface of the solid uneven structure of the mold.

In particular, in order to form a mold-film double-layer emboss structure, according to the present disclosure, air is removed by suction from a rear side (that is, a lower side) of the mold from the space between the surface of the solid uneven structure of the mold which has been heated to a predetermined temperature, for example, between 60 and 85° C. and the outer film. To this end, one or more suction passages penetrated in the vertical direction of the mold are formed. Accordingly, in this mold-film double-layer emboss structure, the zigzag uneven structure of the outer film maintains a close contact with the solid uneven structure of the mold by suction force applied to intake air. And, if this suction force disappears, the contacting state of the zigzag uneven structure of the outer film with the solid uneven structure of the mold 15 easily released.

According to the present disclosure, for the simple design of the suction passage formed by penetrating the mold in vertical direction, the recesses in the mold emboss structure are connected to each other in the lateral direction like a net shape, and a plurality of protrusions are respectively isolated by the recesses of the net shape. In this case, the suction passage provides a communication path with all parts of the recesses, even if it is formed only on a part of the edge of the recesses, for example. If each of recesses are formed in an isolated state, when inhaling the air from the space between the mold embossing structure and the outer film covered thereon to the lower part of the mold, each recess must be provided with a vertical suction passage, respectively. In order to solve this problem, according to the present disclosure, all of the recesses are connected to each other in the lateral direction in a manner that all of the recesses intersect to each other like lines forming a net. Accordingly, the air in the mold recesses of the mold emboss structure can flow in the lateral direction (that is, horizontally), and finally can be discharged by the suction pump along the suction passage through the mold.

As described above, the emboss structure formed on the elastic microcell surface structure according to the present disclosure is formed correspondingly to the emboss structure of the mold. Therefore, the emboss structure is comprised by a plurality of isolated recesses and one protrusion pattern in which a plurality of protrusions are connected to each other in the form of a net.

The elastic microcell surface structure of the present disclosure is provided with a plurality of isolated recesses. When used as a dispensing surface of a cosmetic silicone puff, for example, the plurality of recesses provides receiving portions for accommodating cosmetics similar to the pores of the sponge puff. However, unlike the pores distributed over the entire volume of the existing sponge puff, the microcell recesses according to the present disclosure are formed, for example, at a predetermined depth of about 0.02 to 2.00 mm. The puff according to the disclosure thus provides advantages that cosmetic residue remains less and that the remaining residue can be easily removed by means such as a wipe, so it can be used hygienically.

On the other hand, when a product with the surface structure of the elastic microcell of the present disclosure is used, for example, as a mouse contact surface or wrist contact surface of a mouse pad, the plurality of recesses of the elastic microcell surface structure, provides the effect of reducing the friction between the wrist skin or the bottom portion of the mouse and the surface of the mouse pad, and improving the tactile feeling. Furthermore, even when dust or a foreign substance is clogged in the microcell recesses according to the present disclosure, it can be easily removed by means such as a wet wipe, so it is easy to clean and use hygienically the product.

As described above, according to the present disclosure, in the elastic microcell surface structure in which the outer film is in close contact with the elastomer body, the emboss structure is formed in such a way that the solid uneven structure of the elastomer body is in close contact with the zigzag uneven structure of the outer film. Furthermore, the present disclosure provides a useful emboss structure that has a plurality of isolated desired depth microcell recesses, such as can be used as an dispensing surface for cosmetic silicone puffs or as a surface of a mouse pad. Accordingly, a product such as a silicone puff or a mouse pad having a high-quality elastic microcell surface structure with good tactile feeling and no slippage is generated between the user's skin.

In addition, the silicone puff having the elastic microcell surface structure according to the present disclosure can be provided as a conventional puff product in the form of a disc having one dispensing surface. In addition, the present disclosure can provide various applicator products such as, for example, products in the form of water droplet for dispensing a cosmetic in a narrow gap, or products having applicator surfaces on both sides that a finger or fingers can be interposed therebetween.

As described above, the elastic microcell surface structure according to the present disclosure can be applied as a dispensing surface of an applicator capable of applying a gel or a liquid type cosmetic or a drug to a hand, foot, or face. In addition, the present disclosure can provide various emboss patterns, and can also provide diverse shapes with two dispensing surfaces. Therefore, the present disclosure provides the advantage of being able to construct a group of applicators having an elastic microcell surface structure that can satisfy various consumer needs or preferences.

DETAILED DESCRIPTION OF THE INVENTION

Hereinafter, the present disclosure will be described with reference to the accompanying drawings.

Figure 1A:
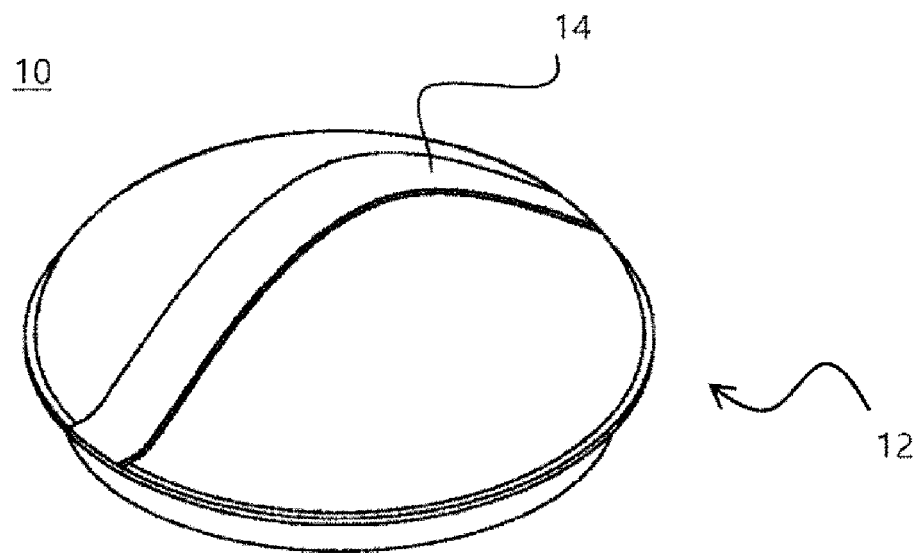
FIGS. 1A to 2C are schematic views for explaining the structure of a conventional cosmetic silicone puff.
Figure 1B:
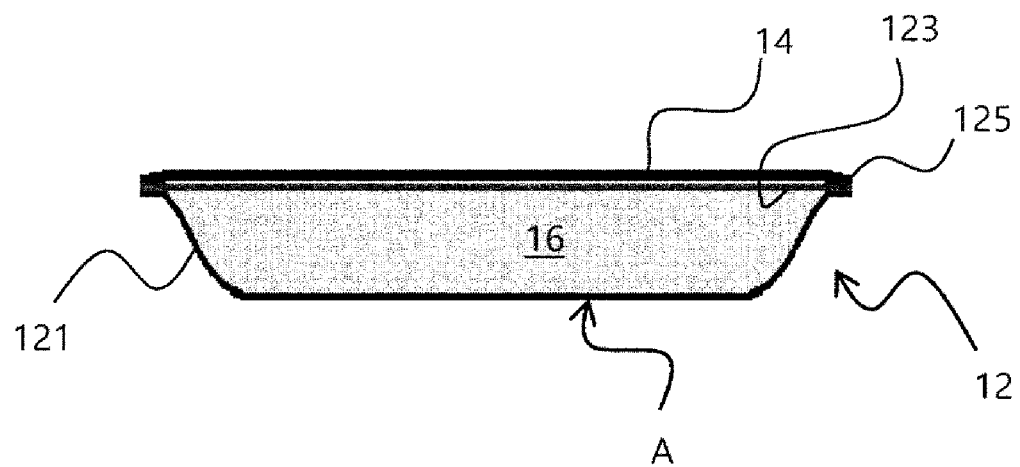

FIG. 1A is a perspective view of a general round disc-shaped cosmetic silicone puff 10, and the cross-sectional structure thereof is schematically illustrated in FIG. 1B. In the illustrated example, the conventional silicone puff 10 includes a skin film 12 made of a thin film of a durable elastic resin material such as Thermoplastic Polyurethane (TPU), for example, a silicone elastic elastomer body 16 made of a high elasticity low hardness silicone rubber material wrapped by the skin film 12, and a ribbon handle 14 that can fit the fingers. The skin film 12 includes a lower skin film 121 surrounding the side surfaces and the lower surface (dispensing surface A) of the elastomer body 16, a upper skin film 123 surrounding the upper surface of the elastomer body 16, and burrs 125 that are the two skin films are heat-sealed by, for example, high-frequency thermal bonding.

The silicone puff 10 may be an cosmetic applicator such that, the user putting fingers in between the ribbon handle 14 and the upper skin film 123, gets cosmetics on the dispensing surface A, and taps or rubs on the skin of the face. In particular, in general, in the silicone puff 10, the thinner the thickness of the skin film 12 of the TPU material is, the soft tactile feeling of the inner silicone elastomer body 16 can be transmitted directly to the skin, which is preferable. For example, the thickness of the skin film 12 may be about 0.01 to 0.10 mm. The silicone puff 10 has a dispensing surface A made of a resin material. Therefore, the silicone puff 10 has various advantages such as a hygienic and almost no discarded cosmetics and a long useful life compared to a sponge puff product.

Figure 2A:
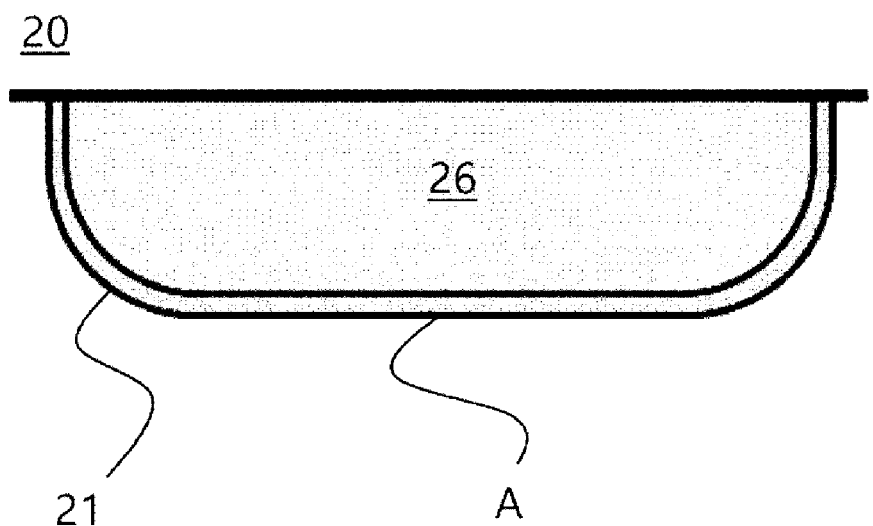

However, as shown in a schematic sectional view in FIG. 2A, the dispensing surface A of the conventional silicon buff 20 may be basically a flat surface without any uneven structure (irregularities. For this reason, there were disadvantages such that liquid or gel-like cosmetics act as a lubricant between the dispensing surface A of the silicone puff 20 and user skin during cosmetic application, resulting in slippage of each other, and the cosmetic ingredients could not properly cover uneven skin area such as pores. In FIG. 2A, reference numeral 26 is an elastomer body made of silicone rubber.

Figure 2B:
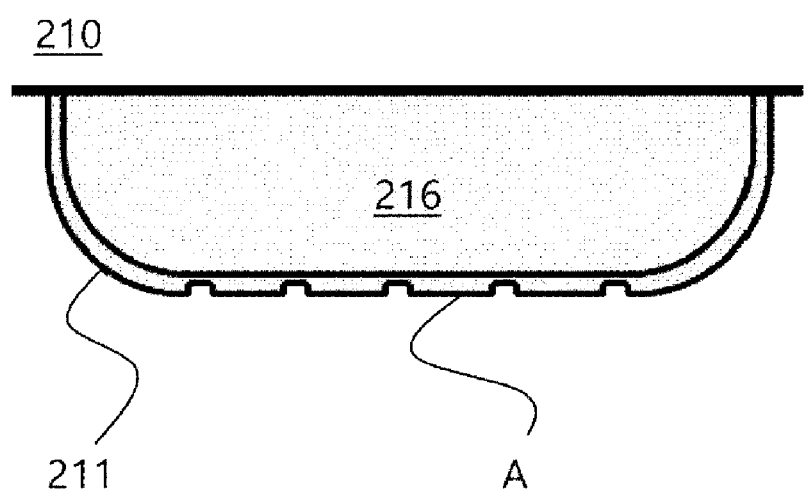

In order to solve this problem in the prior art, as already mentioned, various attempts have been made to form an uneven (irregular) structure, that is, an emboss pattern, on the dispensing surface of the silicon puff. For example, the silicone puff 210 shown in FIG. 2B may be a proposal to form a uneven structure only on the outer surface of the dispensing surface A of the skin film 211 because the elastomer body 216 made of silicone rubber may be not thermally deformed once cured. However, such an uneven structure has a limitation in that since the thickness of the skin film 211 is thin, it is not only difficult to form the uneven structure, but also the cosmetic application function must be limited.

Figure 2C:
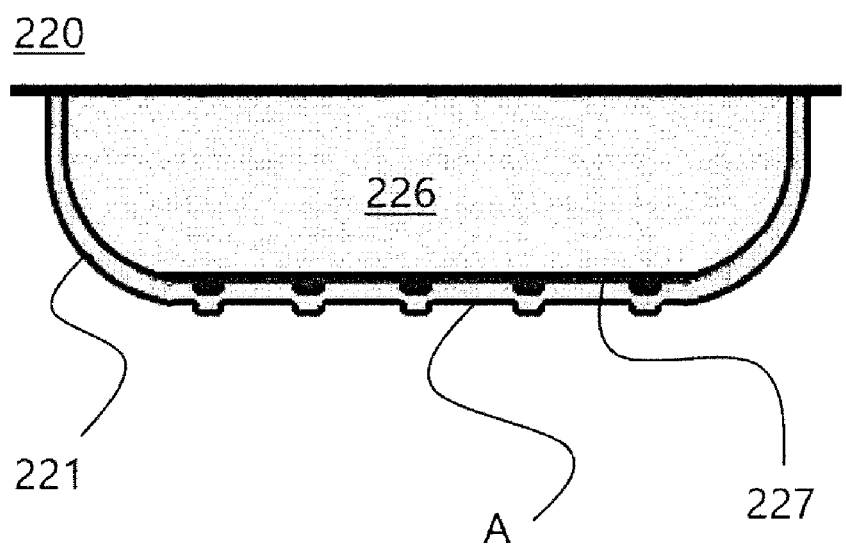

For another example, the silicone puff 220 illustrated in FIG. 2C may be a proposal to form a zigzag-type uneven structure on the dispensing surface A of the skin film 221 surrounding the elastomer body 226 made of silicone rubber. However, such an uneven structure has a weak adhesion between the skin film 221 and the elastomer body 226. For this reason, a separate adhesive layer 227 must be further provided to provide the required adhesion. Therefore, this has a limitation that the manufacturing process may be not only difficult, but also the size of the uneven structure must be limited.

Figure 3:
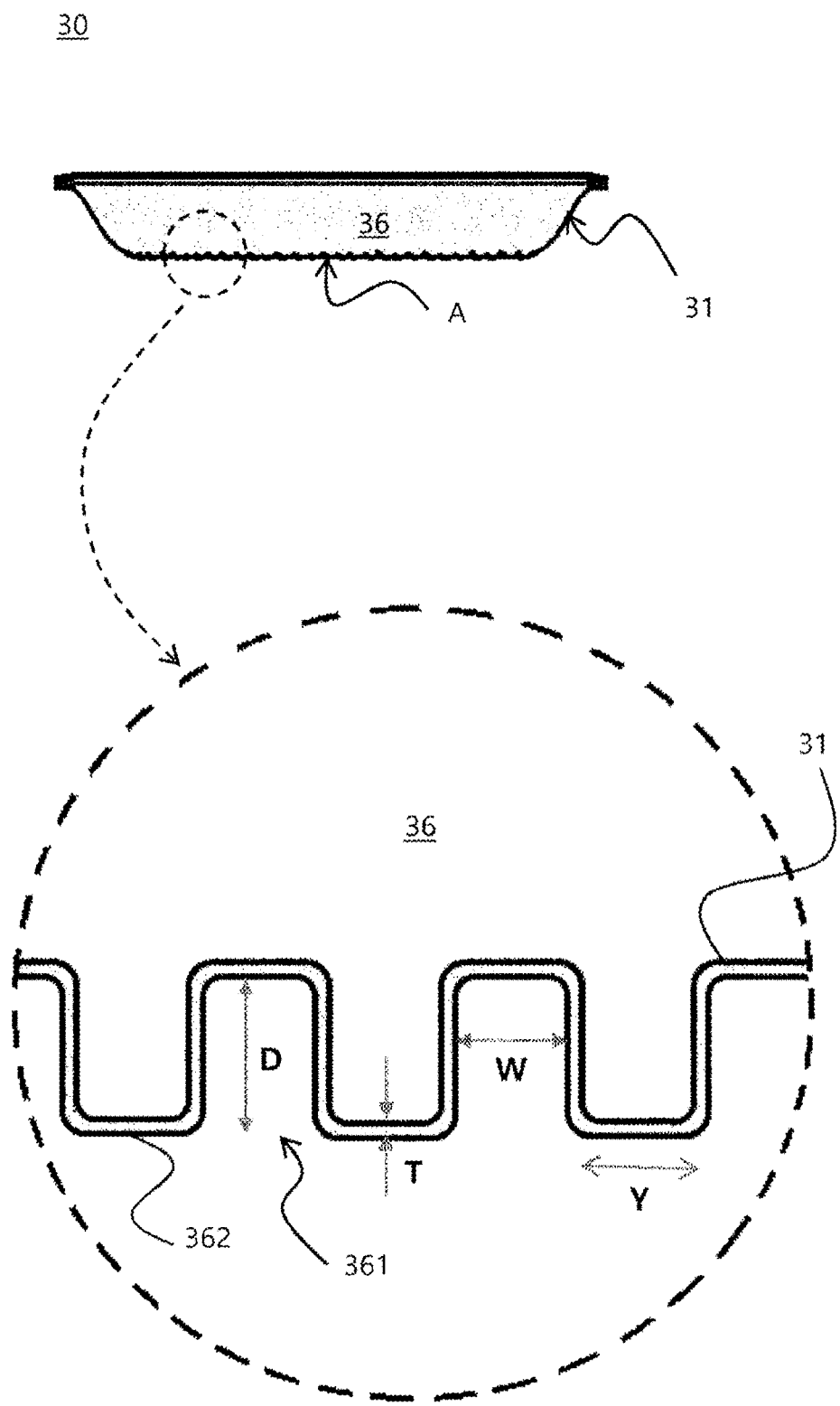
FIG. 3 is a schematic view and a partially enlarged view for explaining a cosmetic silicone puff in the form of a disk as an example having an elastic microcell surface structure according to an exemplary embodiment of the present disclosure.

FIG. 3 is a schematic view for explaining the structure of a silicon puff to which an elastic microcell surface structure according to the present disclosure is applied.

Referring to FIG. 3, a silicon puff 30 in the form of a round disk is shown, which has an elastic microcell surface structure according to the present disclosure, as a dispensing surface A. In the illustrated example, the silicone puff 30 has a shape in which the elastomer body 36 may be wrapped in close contact with the thin outer film 31. In particular, as partially enlarged in the figure, an uneven structure, that is, an elastic microcell surface structure provided according to the present disclosure is formed in the coating surface A.

In particular, in the elastic microcell surface structure according to the present disclosure, the emboss pattern may be formed on both the outer film 31 and the elastomer body 36. Here, the emboss pattern formed on the elastomer body 36 may be in the form of a solid uneven structure in which a plurality of recesses are formed in the surface of the elastomer body. On the other hand, the outer film 31 may be in the form of a zigzag uneven structure formed by alternating bending directions alternately in a manner that the outer film itself is bent and wavy.

In other words, as shown, the elastomer body 36 in the dispensing surface A of the silicon puff 30, have a solid uneven structure including the recesses 361 and the protrusions 362. The outer film 31 may be in close contact with the surface of the solid uneven structure of the elastomer body 36, and as a result, it forms a zigzag uneven structure formed along the surface of the solid uneven structure of the elastomer body 36.

The outer film 31 may be preferably, for example, a thermoplastic and elastic resin such as a thermoplastic polyurethane film. In an exemplary embodiment, the outer film 31 may have a thickness of about 0.01 to 0.10 mm, and preferably a thickness of 0.02 to 0.04 mm. In an exemplary embodiment, it is desirable that the elastomer body 36 provides a skin-like or soft tactile feeling. To this end, the elastomer body 26 may be, for example, a silicone rubber material having a low hardness of about 10 to 45.

As can be seen in the partial enlarged view of FIG. 3, the depth D of the recess 361 (or the height of the corresponding protrusion 362) formed in the surface of the elastomer body 36 may be 2 to 20 times, and preferably about 8 to 15 times or more than the thickness T of the outer film 31. For example, in a specific exemplary embodiment, the thickness T of the outer film may be 0.03 mm, the depth D of the recess 361 may be 0.35 mm, and the width W of the recess 361 may be 0.30 mm. The width W of the recess 361 may be preferably at least four times or more than the thickness of the outer film because the outer film adheres to the side wall of the recess portion 361. The width Y of the protrusion 362 corresponds to the spacing between adjacent recesses 316. The width Y may be not particularly limited, but may be approximately constant over the entire coated surface A for aesthetic or manufacturing convenience, or may have different values depending on the shape or position of the emboss pattern.

As shown, in the dispensing surface A of the silicon puff 30 to which the elastic microcell surface structure provided according to the present disclosure is applied, a solid uneven structure having a plurality of recesses on the surface of the elastomer body 36 is formed. In addition, the outer film 31 serves to protect the surface of the recesses. Therefore, when the user taps the dispensing surface A on the skin of the face, the elastomer body 36 vibrates elastically. Accordingly, cosmetics that have been accommodated in the plurality of recesses can be easily transferred to the facial skin. In addition, an emboss structure composed of a plurality of recesses and protrusions shaped like a mesh can provide friction. Therefore, when applying the cosmetic to the skin, the advantage of being able to keep the good tactile feeling of the silicone constant without slipping is provided.

FIGS. 4A to 4D are schematic flow views for explaining a characteristic manufacturing process using a mold-film double layer emboss structure in an elastic microcell surface structure according to an exemplary embodiment of the present Disclosure.

Figure 4A:
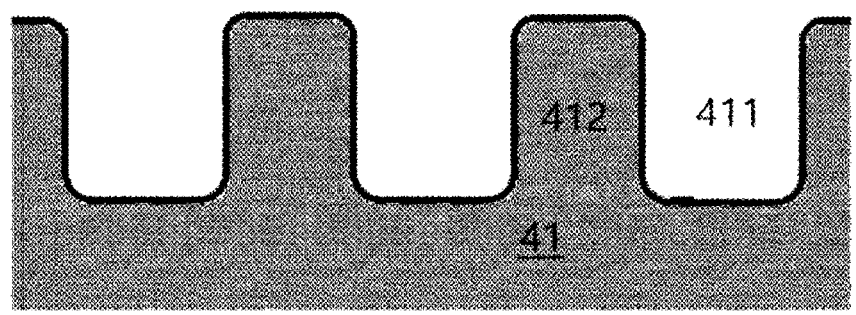
FIGS. 4A to 4D are schematic flow views for explaining a manufacturing process through a mold-film double layer embossing structure in the process of manufacturing an elastic microcell surface structure according to an exemplary embodiment of the present disclosure.

FIG. 4A shows a solid uneven structure of the mold for manufacturing an elastic microcell surface structure according to the present disclosure. On the inner surface of the cavity of the mold 41, an emboss pattern of a solid uneven structure for forming emboss, that is, recesses 411 and protrusions 412 are formed. Here, a recess 411 may be characterized in that it may be connected with adjacent recesses 411 in a manner in which air flows laterally. In other words, as will be further described with reference to FIG. 5 below, the recesses 411 are preferably connected to each other in a manner that air can flow laterally in the form of one continuous shape like a net. And, the protrusions 412 are formed as a plurality of individual protrusions separated from the lateral direction in all directions by the net-shaped recesses 411.

Figure 4B:
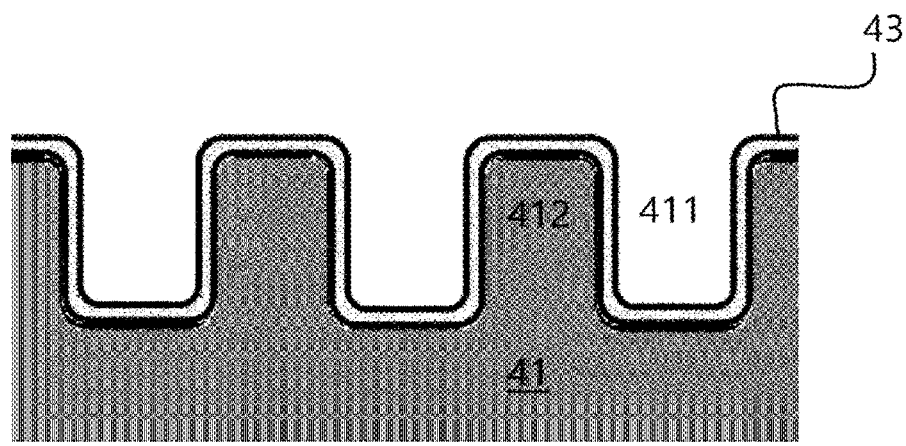

FIG. 4B shows a state in which the outer film 43 may be closely adhered along the surfaces of the protrusions 412 and the recesses 411 of the mold 41. After the outer film 43 covers the protrusions 412, in order to be inserted into and closely adhered on the surface of recesses 411, the air in the recesses 411 must be removed. According to the present disclosure, the air of the recesses 411 may be removed by forcibly sucking through a suction passage (not shown) communicating in the lateral or lower direction of at least a portion of the recesses 411. Accordingly, the outer film 43 may be physically pulled to and to be in close contact with the surfaces of the recesses 411 between the protrusions 412 of the mold 41.

The outer film 43 may be preferably an elastic resin film, such as a thin film made of a thermoplastic polyurethane material. In this case, the mold 41 may be preferably heated to the glass transition temperature of, for example, a thermoplastic polyurethane film, so that the outer film 43 can be more easily adhered to the surfaces of the recesses 411 and the protrusions 412 of the mold. In particular, it is preferable to be heated to a temperature that allows the film to be deformed as much as necessary and bent into the recesses 411 without being excessively melted by being kept at a lower temperature among the glass transition temperatures.

When the outer film 43 may be in close contact with the surface of the mold 41 by heat and suction pressure, as a result, the outer film 43 has a form of a zigzag uneven structure in close contact with the surface of the recess portion 411 and the protruding portion 412, that is, the solid uneven structure of the mold 41. And accordingly, the mold 41 and the outer film 43 are seen as if forming an uneven structure. In this specification, it is referred to as a "mold-film double layer emboss structure".

Figure 4C:
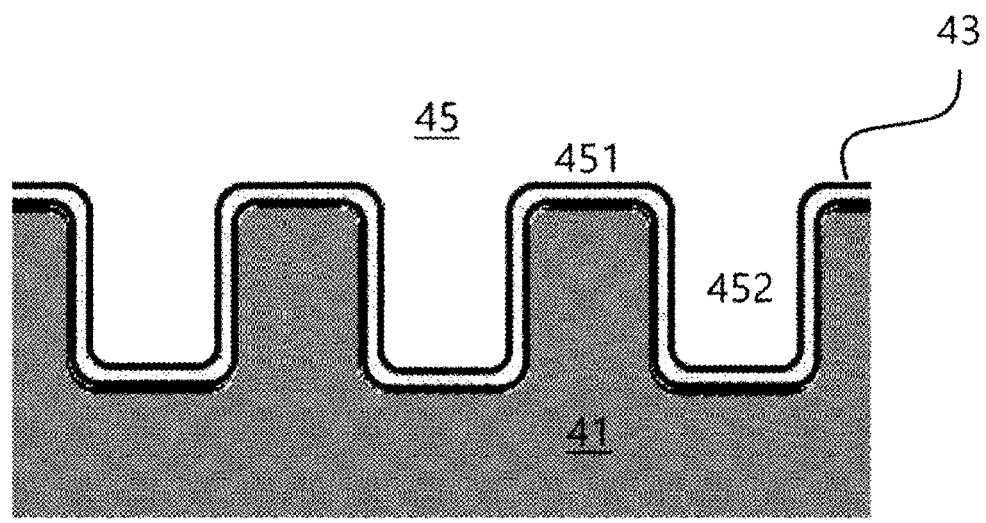

FIG. 4C shows a state in which a liquid elastomer composition, such as a silicone rubber liquid, may be introduced on the mold-film double layer emboss structure shown in FIG. 4B. Accordingly, a solid uneven structure, that is, recesses 451 and protrusions 452 may be formed in the surface of the elastomer body 45 in a shape corresponding to the recesses and the protrusions of the mold-film double layer emboss structure.

At this time, the shapes of the recesses 451 and the protrusions 452 of the elastomer body 45 correspond to the shapes of the recesses and protrusions of the elastic microcell surface structure.

Therefore, the recesses 451 of the elastomer body 45 are formed of a plurality of individual recesses that are isolated from each other similar to the projections 412 of the mold 41, and the projections 452 of the elastomer body 45 are formed of a continuous protrusions connected to each other in the form of a network similar to the recesses 411 of the mold 41. As a result, a solid uneven structure having a shape corresponding to the solid uneven structure of the mold 41 may be formed on the surface of the elastomer body 45.

Figure 4D:
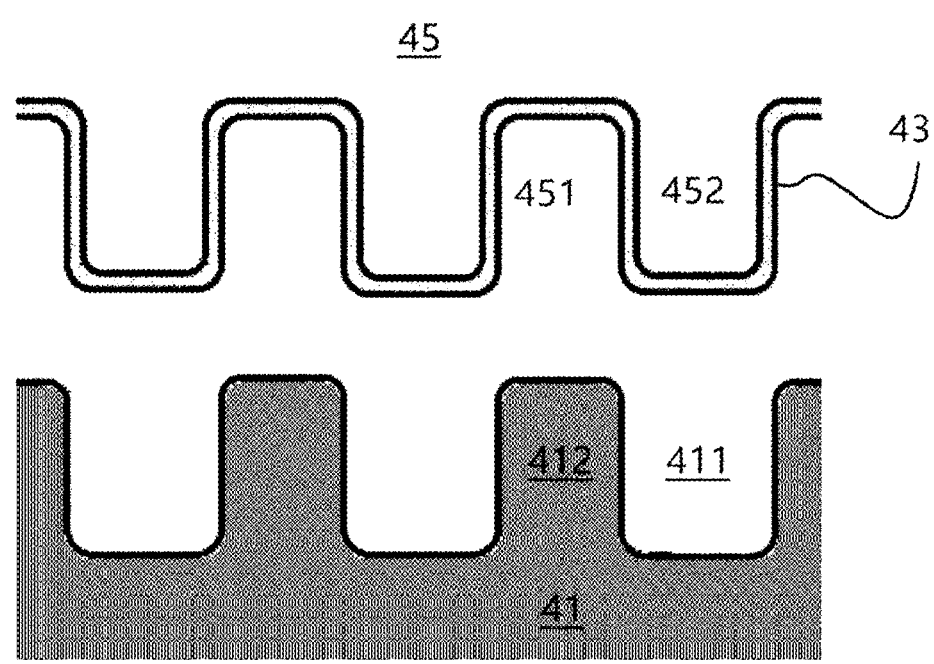

FIG. 4D shows a process of removing the suction pressure and separating the elastomer body 45 from the mold 41 after the liquid elastomer body 45 introduced in FIG. 4C is cured. As shown, in this case, the outer film 43 may be detached from the mold 41 in a state of being adhered to and attached to the surface of the elastomer body 45. The outer film 43 was in close contact with the mold 41 by suction pressure in FIGS. 4B and 4C. Then, while the liquid elastomer body 45 is cured, the outer surface of the elastomer body 45 may be adhered to the surface of the elastomer body 45 by the viscosity of the elastomer body surface itself and the heat applied during the curing process. Then, when the suction pressure disappears, the outer film 43 may be separated from the mold 41 while being attached to the surface of the elastomer body 45.

Figure 5:
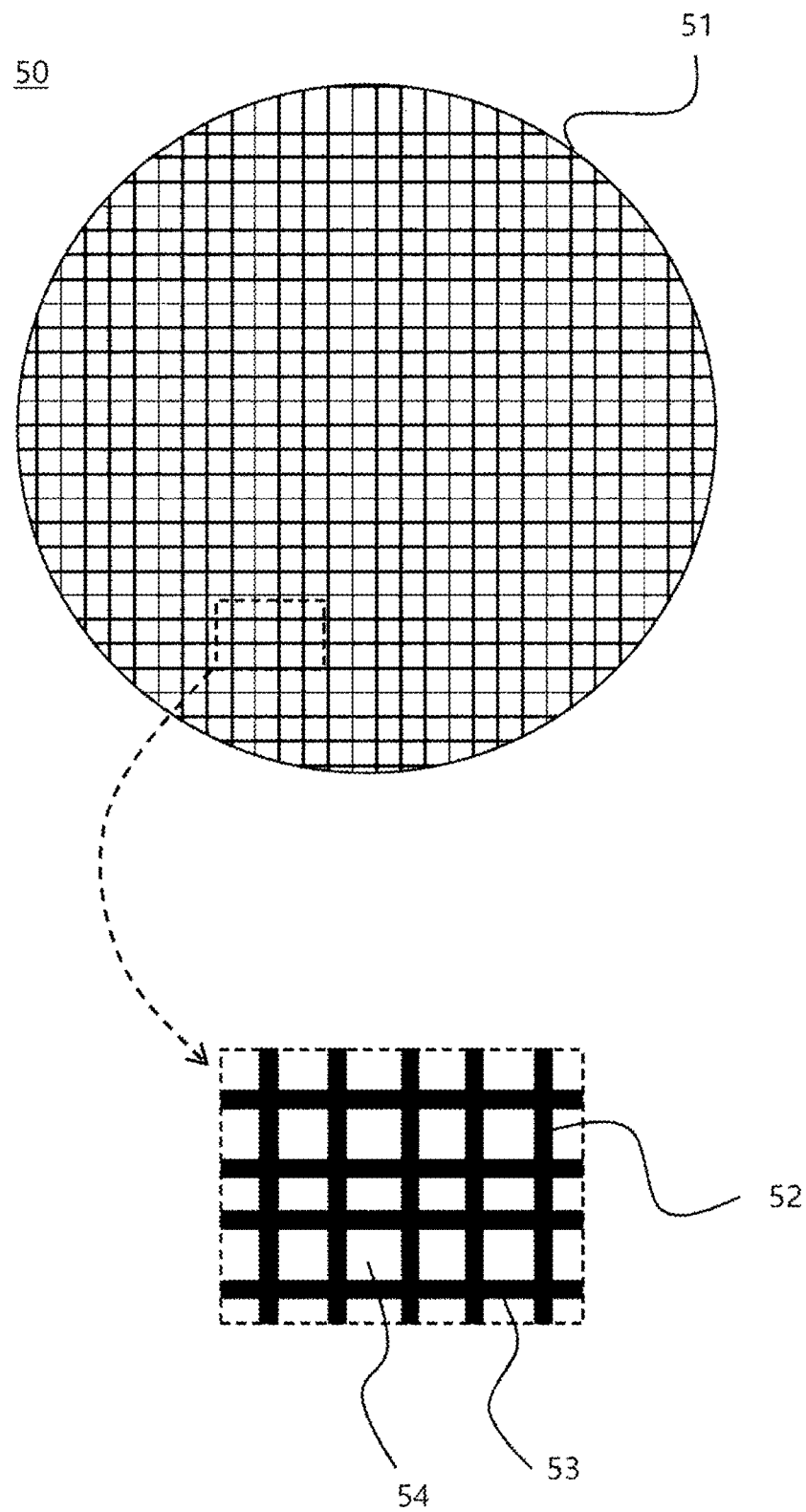
FIG. 5 is a schematic view for explaining an example of an emboss pattern of an elastic microcell surface structure according to an exemplary embodiment of the present disclosure.
Figure 6A:
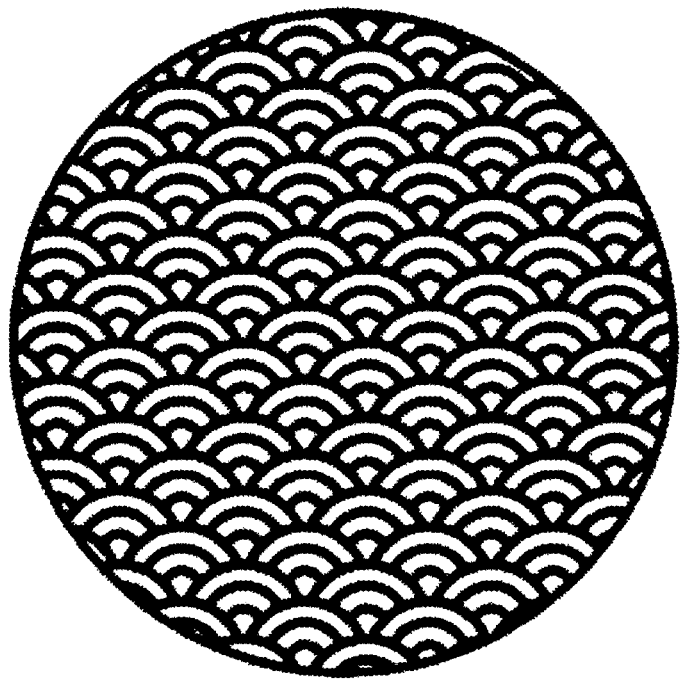
FIGS. 6A to 6F are schematic views showing various examples of emboss patterns of an elastic microcell surface structure according to exemplary embodiments of the present disclosure.
Figure 6B:
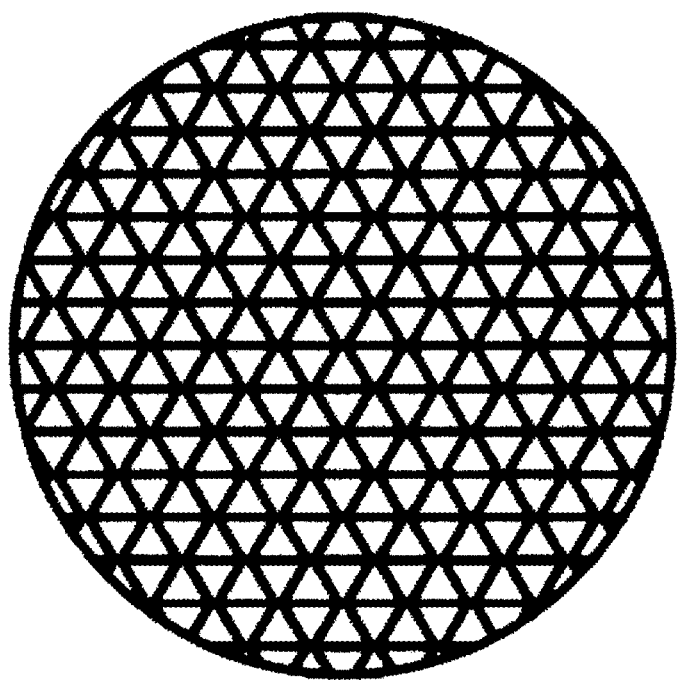
Figure 6C:
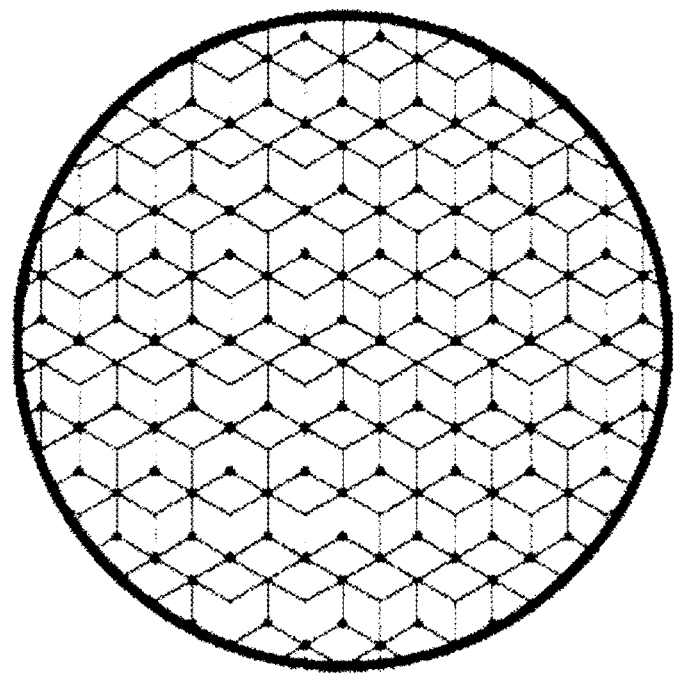
Figure 6D:
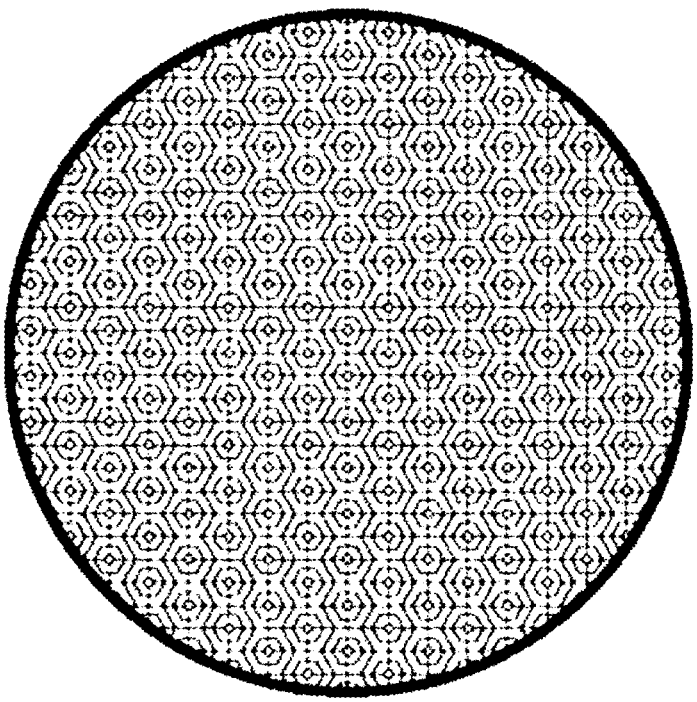
Figure 6E:
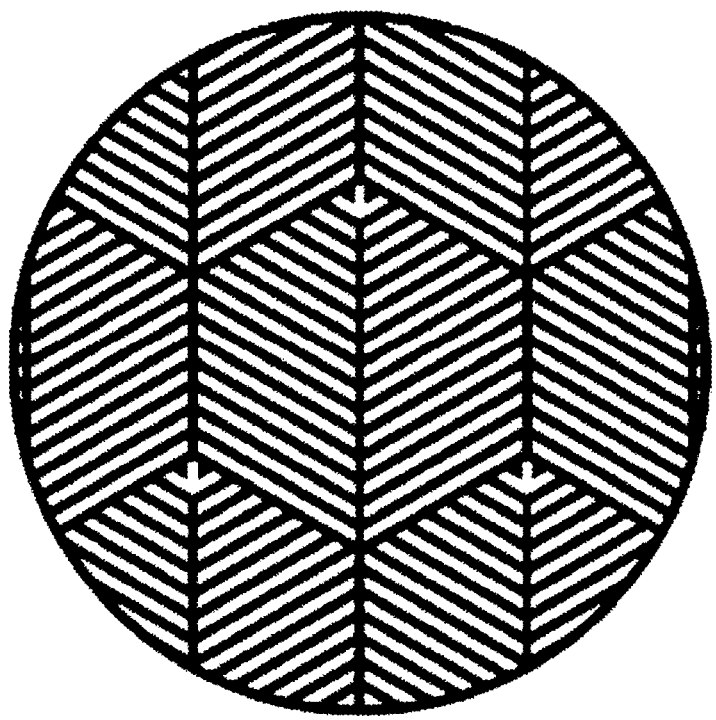
Figure 6F:
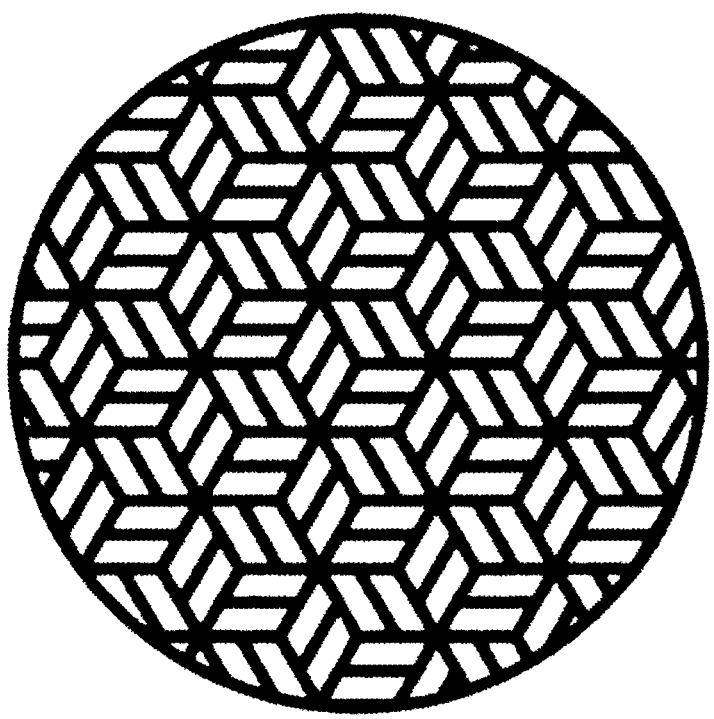

FIG. 5 is a schematic plan view for explaining a pattern of recesses and protrusions of an elastic microcell surface structure according to an exemplary embodiment of the present disclosure.

Referring to FIG. 5, the illustrated pattern illustrates a grid pattern composed of a plurality of parallel straight lines orthogonal to each other in a circle. In this case, in the illustrated pattern, the circular edge line 51 and the straight lines 52 and 53 orthogonal to each other represent protrusions connected to each other in a form of a network. In addition, a plurality of recesses 54, which are isolated from each other by projections, are represented by white spaces surrounded by black lines in the drawing.

FIGS. 6A to 6F are schematic views showing emboss patterns composed of recesses and protrusions of an elastic microcell surface structure according to exemplary embodiments of the present disclosure.

As shown, the emboss patterns can be configured in various forms. In the emboss pattern of the elastic microcell surface structure which can be produced according to the present disclosure, the protrusions made of black lines are all connected to each other in the form of one mesh. As a result, a plurality of individual recesses made of white parts surrounded by black lines are each separated by protrusions. The shape of the pattern may be not particularly limited and may be variously configured. As illustrated in FIGS. 6A to 6F, any shape is possible, including, for example, a honeycomb structure, a comb pattern, an irregular shape, a specific character shape, etc., as well as a lattice structure.

Figure 7:
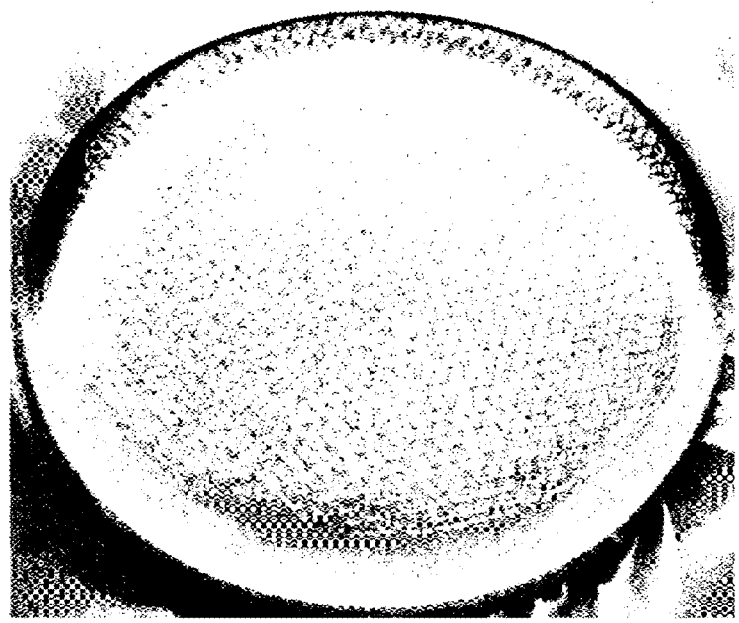
FIGS. 7 and 8 are sample photos showing examples of the elastic microcell surface structure of disk-shaped silicon puffs, according to exemplary embodiments of the present disclosure.
Figure 8:
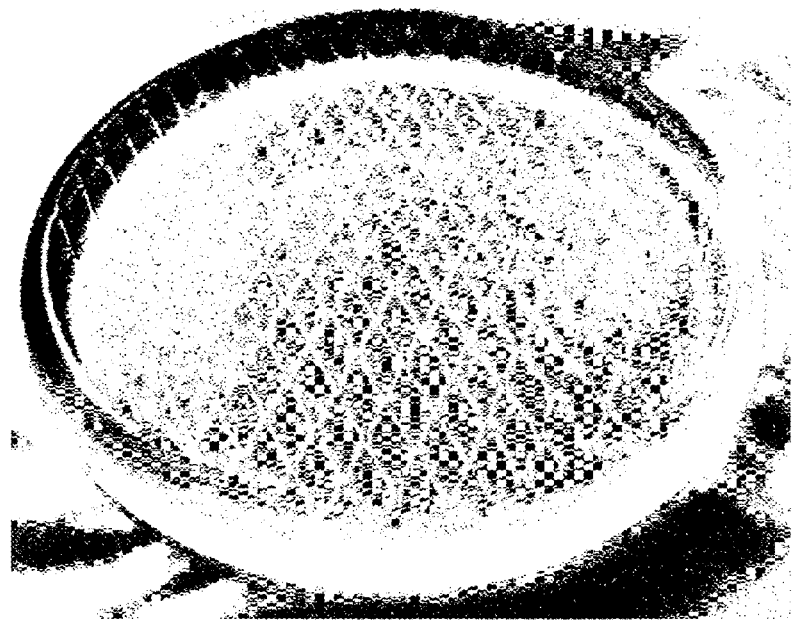

FIGS. 7 and 8 are sample photos showing examples of cosmetic applicators, that is, silicone puffs, applied to dispensing surfaces of elastic microcell surface structure according to an exemplary embodiment of the present disclosure. It can be seen that the protrusions in the uneven structure of the samples of the illustrated silicon puff are continuous in the form of a mesh.

Figure 9:
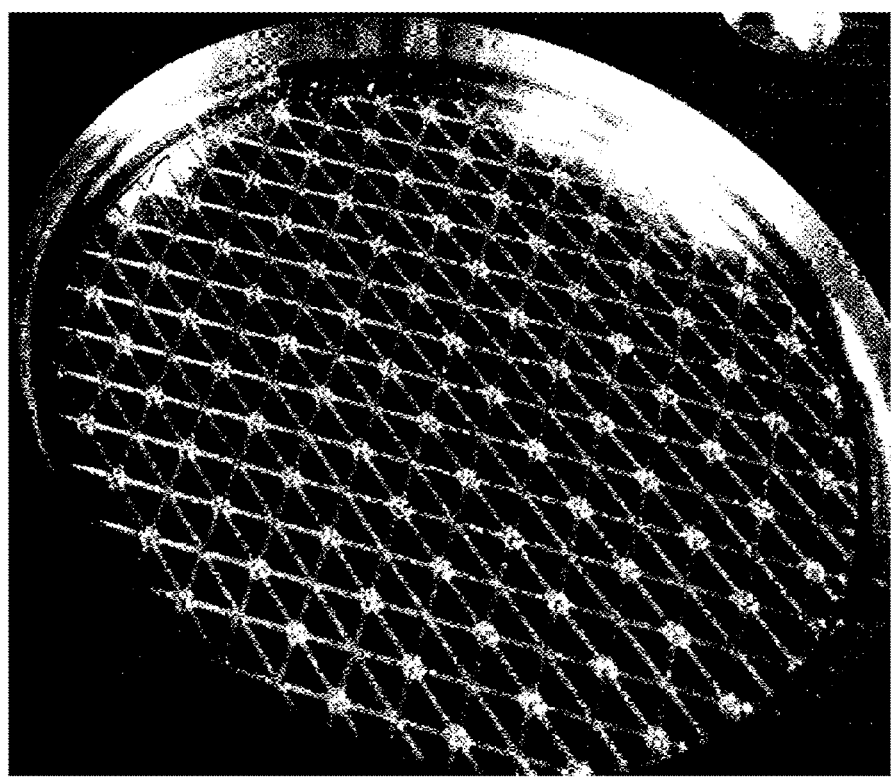
FIG. 9 is a mold sample photo for the fabrication of an elastic microcell surface structure according to an exemplary embodiment of the present disclosure.

FIG. 9 is a sample photo showing an emboss pattern for the production of a silicone puff applying an elastic microcell surface structure to a dispensing surface according to an exemplary embodiment of the present disclosure. As shown, in the emboss pattern, it can be seen that, in a manner corresponding to the dispensing surface pattern of the silicon puff, the recesses are continuously formed in a mesh shape, and a plurality of protrusions are separated by the recesses.

Figure 10:
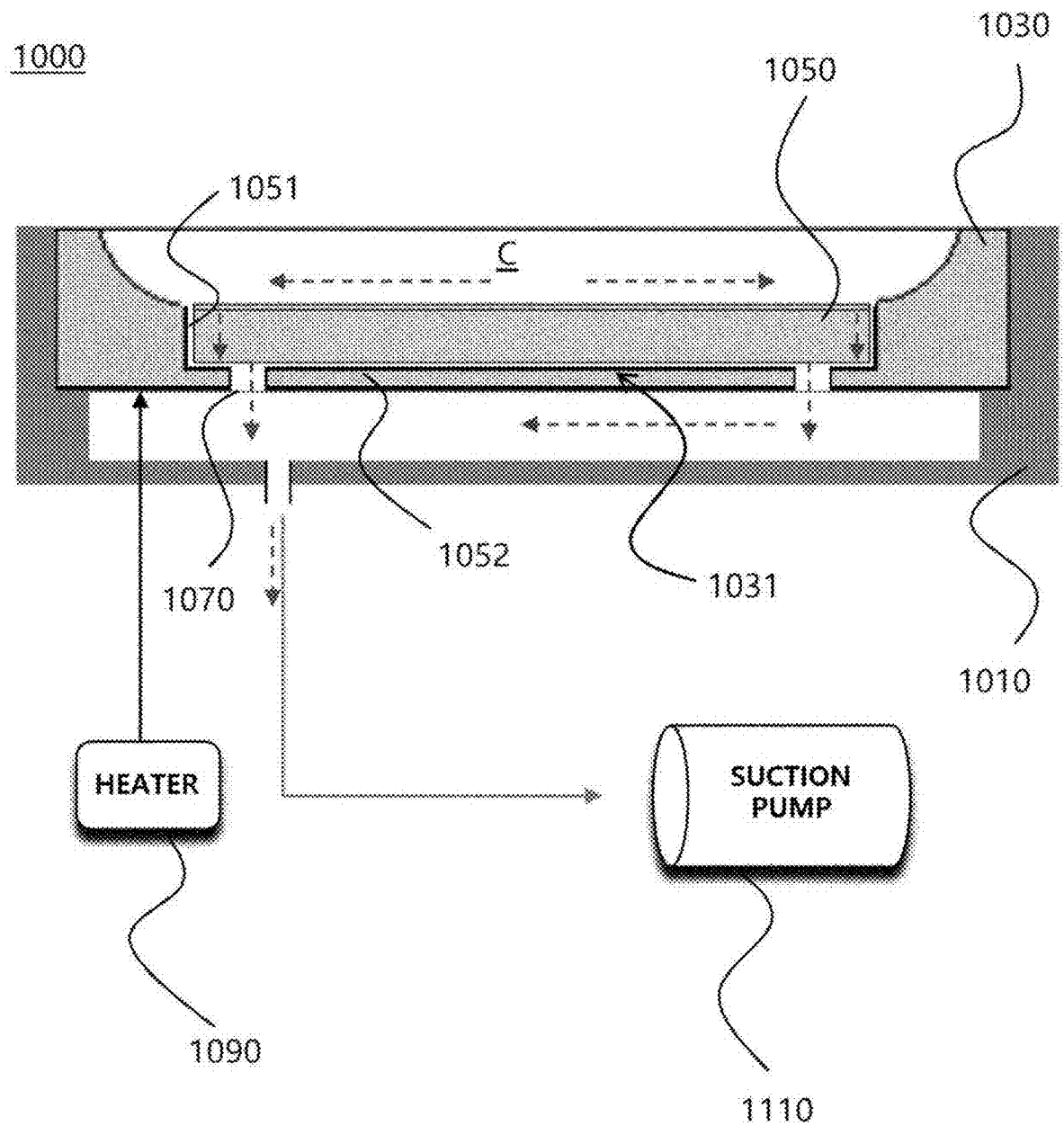
FIG. 10 is a schematic cross-sectional view illustrating the configuration of an apparatus for manufacturing an elastic microcell surface structure according to an exemplary embodiment of the present disclosure.

FIG. 10 is a schematic cross-sectional view illustrating a configuration of a silicon puff manufacturing apparatus applying an elastic microcell surface structure to a dispensing surface according to an exemplary embodiment of the present disclosure.

Referring to FIG. 10, the illustrated manufacturing apparatus 1000 comprises a mold member (comprising 1030 and 1050) for defining the cavity C; a suction path 1070 penetrating in the vertical direction from the mold member as a passage for inhaling air; a heater 1090 capable of maintaining the mold member at a predetermined temperature; and a suction pump 1110 connected to the suction passage for forcibly sucking air.

The mold member (comprising 1030 and 1050) may be a member seated on the jig 1010 of the manufacturing worktable, and may be desirable to be made of a durable metal material such as aluminum, brass, and stainless steel to facilitate heat transfer to the material molded in the cavity C. However, it is not necessary to be limited to this, and it is possible to manufacture various materials. Although in the illustrated example, an example of forming the mold member (comprising 1030 and 1050) may be assembled by a mold base 1030 and a pattern member 1050 separately manufactured, but it is also possible to manufacture them integrally as one component.

In the preferred exemplary embodiment shown, the mold member (comprising 1030 and 1050) may be fabricated into an assembly type that combines a mold base 1030 and a pattern member 1050. The mold base 1030 may define a shape of one or more cavities C, and may include a seating portion 1031 for seating the pattern member 1050 on the lower surface of each cavity C. The pattern member 1050 may be a member having a uneven structure or an emboss pattern of a predetermined shape on one or both surfaces, and may be inserted into the seating portion 1031 of the mold base 1030 to form a lower surface of the cavity C.

A heater 1090 may be an electric heater connected to supply heat energy to the jig 1010 or the mold member (comprising 1030 and 1050), particularly to the mold base 1030.

A suction passage 1070 penetrates the lower surface of the seating portion 1031 of the mold base 1030 in vertical direction. In addition, the suction passage 1070 may be an air hole structure that communicates a particular recess of the emboss pattern formed on the pattern member 1050 at one end, and communicates the suction pump 1110 at the other end, so as to suck air from the pattern member 1050 to the suction pump 1110. The number and shape of the holes constituting the suction passage 1070 may be variously implemented according to exemplary embodiments.

A side gap 1051 and a bottom gap 1052 exist between the pattern member 1050 and the seating portion 1031 of the mold base 1030. The side gap 1051 may be a gap between the side surface of the pattern member 1050 and the sidewall surface of the seating portion 1031 adjacent thereto. In addition, the lower gap 1052 may be a gap between the lower surface of the pattern member 1050 and the bottom surface of the seating portion 1031 adjacent thereto. In order to secure a space for the lower gap 1052, a predetermined uneven structure may be formed at the bottom of the pattern member 1050. In this case, the air of the emboss pattern structure on the upper surface of the pattern member 1050 can easily flow to the lower side of the mold base 1030 through the side gap 1051 and the lower gap 1052, and accordingly, the structure of the suction passage 1070 formed in the mold base 1030 can be simplified, and an advantage of good suction efficiency can be provided.

According to the manufacturing apparatus 1000, an outer film is disposed on the cavity C. Thereafter, the edge of the outer film is pressed and sealed along the edge of the mold base 1030, and then the suction pump 1110 is operated. Then, the air in the cavity C is discharged to the suction passage 1070 through the side gap 1051 and the lower gap 1052 of the pattern member 1050. As a result, the outer film may be in close contact with surfaces of the recesses and protrusions of the emboss pattern formed on the upper surface of the pattern member 1050.

In addition, at the same time as applying suction pressure using the suction pump 1110, the heater 1090 may be operated to supply heat to the mold base 1030. For example, in the case of a thermoplastic polyurethane film having an outer film thickness of 0.03 mm, it can be heated to about 70~95° C.

As a result, because in the emboss pattern of the pattern member 105, the recesses are a continuous recess portion connected to each other in the form of a mesh in the lateral direction, and because the size of a recess (that is, depth and width of a recess) may be greater than the thickness of the outer film (2 or 4 times or more), and because the outer film itself may be an elastic polyurethane film and may be heated to a predetermined temperature, the outer film may be closely adhered along the surfaces of the recesses and protrusions of the emboss pattern of the pattern member 1050 to form a zigzag uneven structure. As a result, a mold-film double layer emboss structure may be formed as described above with reference to FIG. 4.

While maintaining the air suction pressure by the suction pump and the heating state, a liquid silicone rubber-like elastic composition may be introduced into the cavity C on the mold-film double-layer emboss structure. The cavity C may be filled while filling the recesses of the mold-film double-layer emboss structure. Then, the liquid elastomer composition filled in the cavity C has a shape corresponding to the shape of the cavity C as well as the recesses and protrusions of the mold-film double layer emboss structure.

In this state, the suction pressure by the suction pump and heating state are maintained until the liquid silicone rubber is cured, for example, for 1 to 5 minutes. Then the silicone rubber component may be cured, resulting manufacture of a product having an elastic microcell surface structure, which may be composed of an elastomer body in which a solid uneven structure corresponding to the emboss pattern of the pattern member 1050 may be formed, and an outer film that may be in close contact with the surface of the solid uneven structure of the elastomer body to form a zigzag uneven structure.

Figure 11:
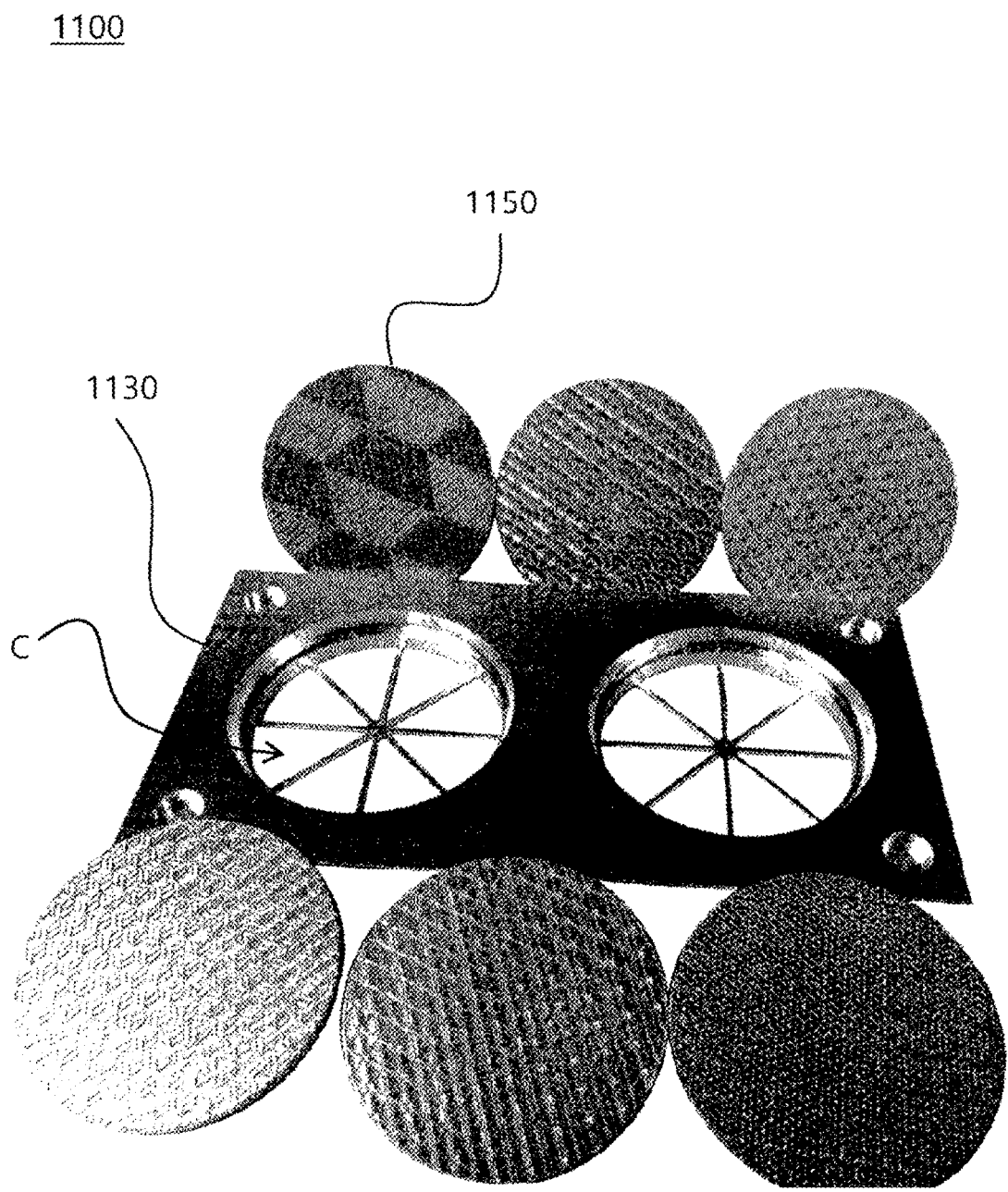
FIG. 11 is a sample photo illustrating an assembly-type mold member in an apparatus for manufacturing an elastic microcell surface structure according to an exemplary embodiment of the present disclosure.

FIG. 11 is a sample photo showing an example of an assembly type mold member in the manufacturing apparatus of the elastic microcell surface structure according to an exemplary embodiment of the present disclosure.

Referring FIG. 11, a sample of the assembled mold member 1100 is illustrated. In this example, the assembled mold member 1100 includes a mold base 1130 and a pattern member 1150. Although the mold base 1130 is illustrated as having two cavities C, however, it is obvious that the number of cavities C of the mold base of the present disclosure may be one, or may be formed more than two. Meanwhile, in the drawing, six pattern members 1150 having different emboss patterns that can be disposed in the cavity C of the mold base 1130 are illustrated. However, it is apparent that the pattern member 1150 can be manufactured in more various ways.

In the illustrated example, the shape of the cavity C defines a disc shape for manufacturing a disc-shaped product. However, the present disclosure is not limited to such a disc-shaped product. The present disclosure includes products having various shapes such as a square, an oval, a droplet, a predetermined character, etc., and correspondingly, the shape of the cavity C may also vary, which will be obvious to those with knowledge in the technical field. In addition, depending on the shape and size of the cavity C, not only a small product such as a cosmetic silicone puff, but also a relatively large size product such as a mouse pad can be manufactured.

An assembled mold member 1100 according to the illustrated example shows that the pattern member 1150 may be manufactured and assembled separately from the mold base 1130. According to this, while replacing various types of pattern members 1130, a convenient manufacturing apparatus can be provided in a small amount in a variety of ways.

Figure 12:
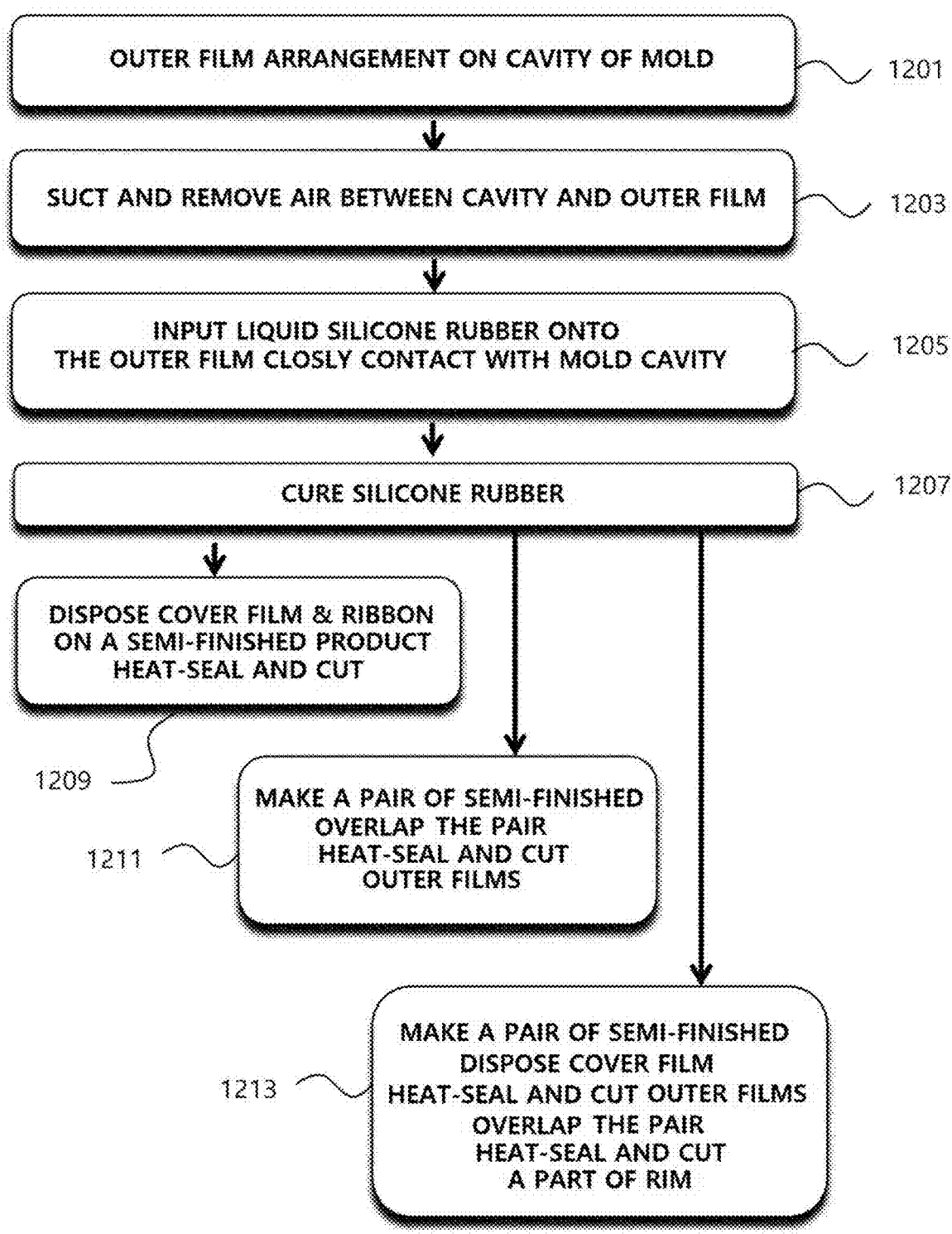
FIG. 12 is a schematic flow chart showing the steps of the method of manufacturing an elastic microcell surface structure according to an exemplary embodiment of the present disclosure.

FIG. 12 is a schematic flowchart showing steps of a method for manufacturing an elastic microcell surface structure according to an exemplary embodiment of the present disclosure, and FIGS. 13 to 17 are schematic diagrams further illustrating in detail steps of a method for manufacturing an elastic microcell surface structure according to an exemplary embodiment of the present disclosure It Referring to FIG. 12, a method for manufacturing an elastic microcell surface structure 1200 according to an exemplary embodiment of the present disclosure includes an outer film arrangement step 1201, a mold-film double layer emboss structure formation step 1203, and a liquid silicone rubber input step 1205, curing step 1207, and finishing steps (comprising steps 1209, 1211, and 1213).

Figure 13:
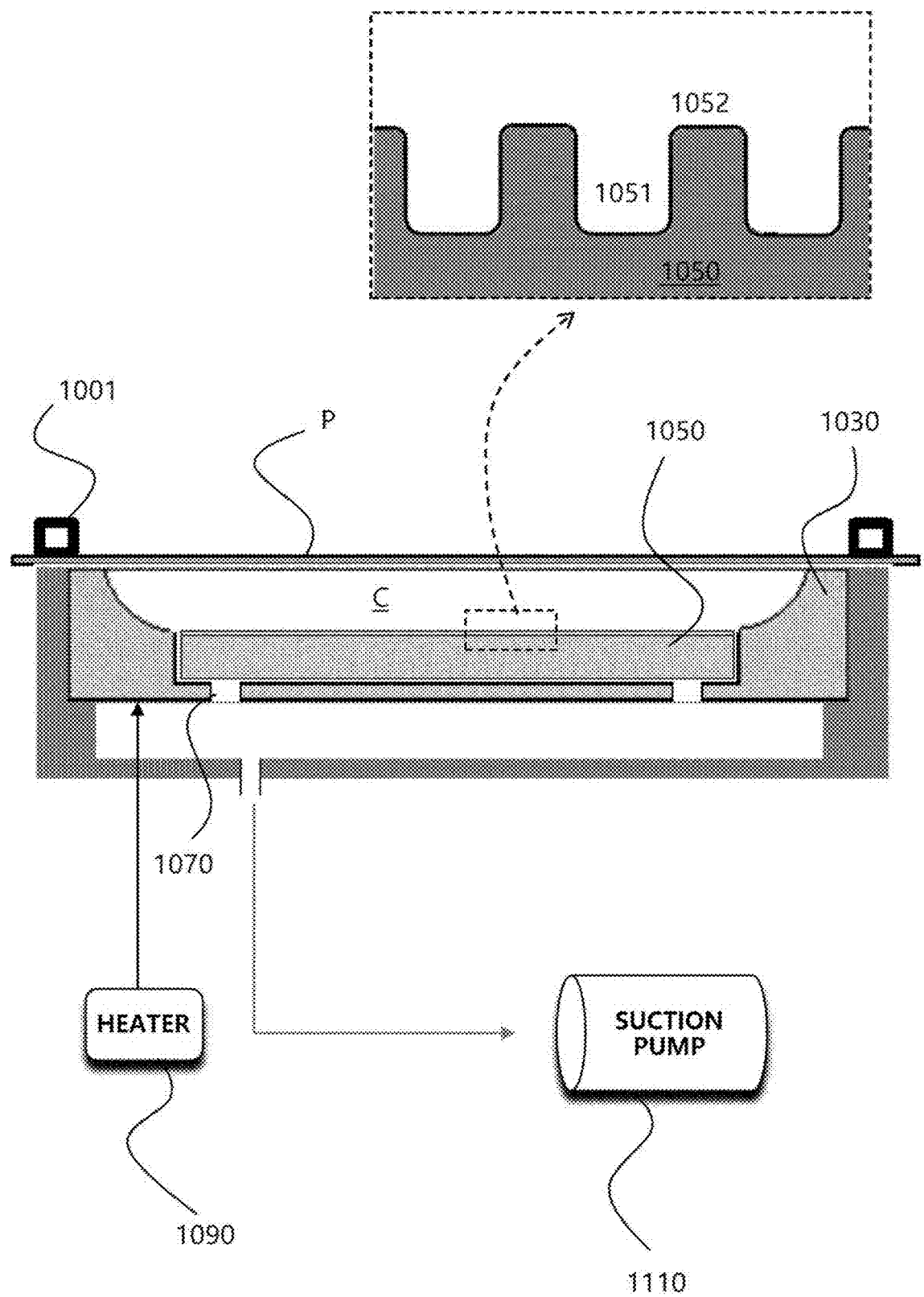
FIG. 13 is a schematic view showing a step of a method for manufacturing an elastic microcell surface structure according to another exemplary embodiment of the present disclosure.

An outer film arrangement step 1201 is a step of disposing the outer film on the cavity of the mold member of the manufacturing apparatus as described above with reference to FIGS. 10 and 11. An emboss pattern may be formed on the bottom surface of the cavity of the mold member. For example, the emboss pattern may have a structure including recesses continuously connected in a network shape formed on an upper surface of the pattern member 1050 and a plurality of protrusions separated by the recesses. This step is shown in more detail in FIG. 13. Referring to FIG. 13, in the method for manufacturing the elastic microcell surface structure 1200, a step 1201 of disposing an outer film on the mold cavity C is illustrated.

In the illustrated step, for example, a 0.03 mm thick TPU material outer film P may be disposed on the upper surface of the cavity C of the mold member (1030 and 1050). Then, the edge of the outer film P may be fixed using the pressing member 1001 so that the outer film P may be tightened in a horizontal state. Accordingly, the upper portion of the cavity C space, that is, the outer film P side can be sealed so that the air could not escape.

Figure 14:
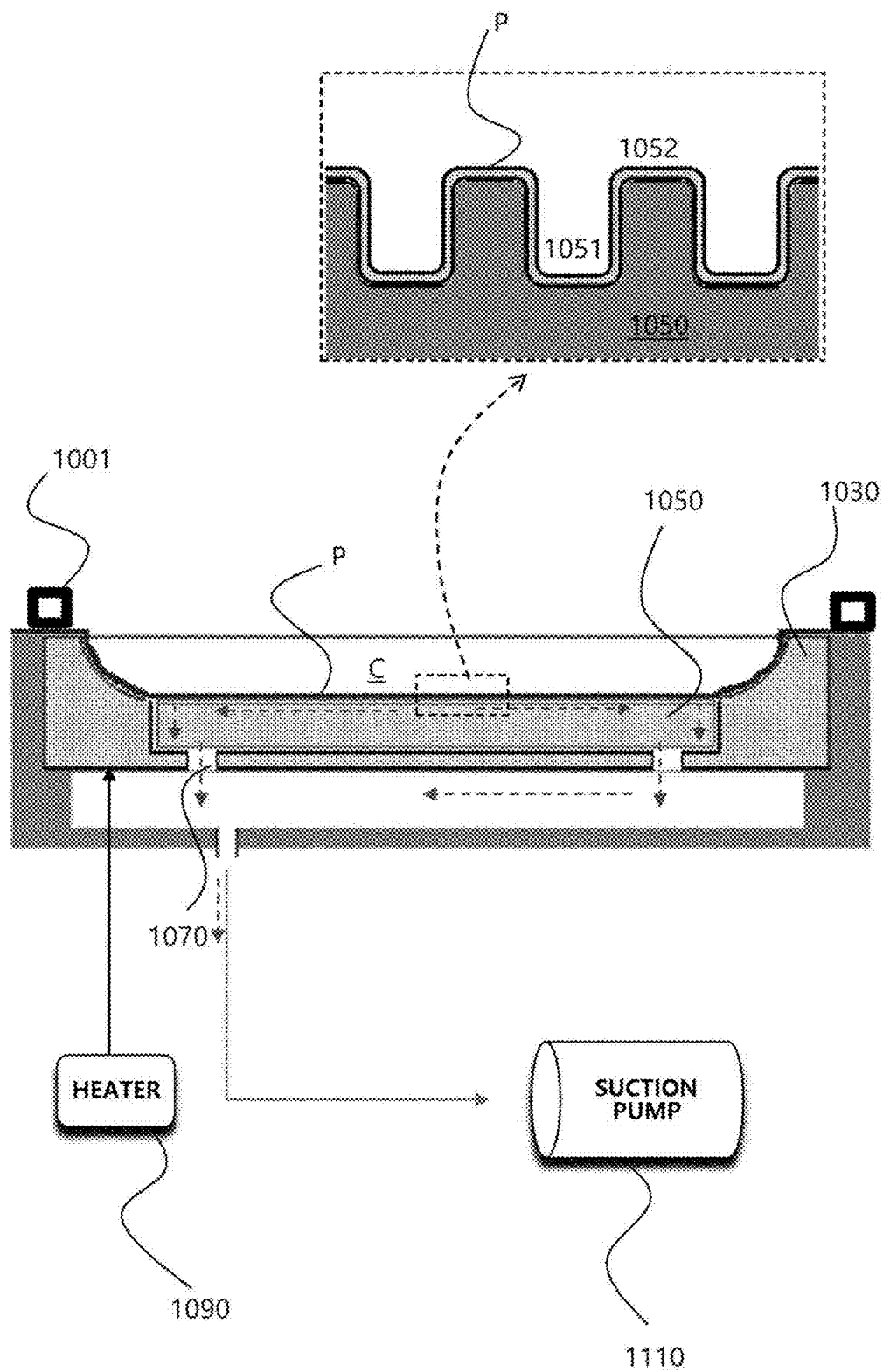
FIGS. 14 to 17 are schematic views showing in more detail the steps of the method for manufacturing an elastic microcell surface structure according to an exemplary embodiment of the present disclosure.

In the mold-film double layer emboss structure forming step 1203, the air in the cavity C space is sucked by operating the suction pump 1110. As a result, the outer film P is in close contact with the lower surface of the cavity C, that is, the emboss pattern surface of the pattern member 1050. This step is shown in more detail in FIG. 14. Referring to FIG. 14, a step 1203 of forming a mold-film double layer emboss structure is illustrated in a method 1200 for manufacturing an elastic microcell surface structure according to the present disclosure.

In the illustrated step, the heater 1090 heats the mold member (1030 and 1050). The heated mold member (1030 and 1050) may heat the outer film P to its glass transition temperature or lower, for example, 75° C. At the same time, the suction pump 1110 operates to suck air in the cavity C through the suction passage 1070. Then, the air in the mold cavity C, which is in a sealed state by the outer film P, may be discharged to the suction pump 1110 side through the suction passage 1070. As the air escapes from the cavity C, the outer film P increases and bends locally as it is heated due to its own elasticity and the temperature of the mold member. Accordingly, the outer film may be in close contact with the lower surface of the mold cavity, that is the surfaces of the recesses and protrusions of the mold emboss pattern. In this way, a mold-film double-layer emboss structure may be formed on the lower surface of the cavity C by forming a zigzag uneven structure of the outer film in close contact with the surface of the solid uneven structure of the emboss pattern.

At this time, in order to improve the adhesion of the outer film P, the depth and width of the recesses 1051 of the mold emboss pattern are at least 2 times and 4 times larger than the thickness of the outer film, preferably about 8~15 times larger.

Figure 15:
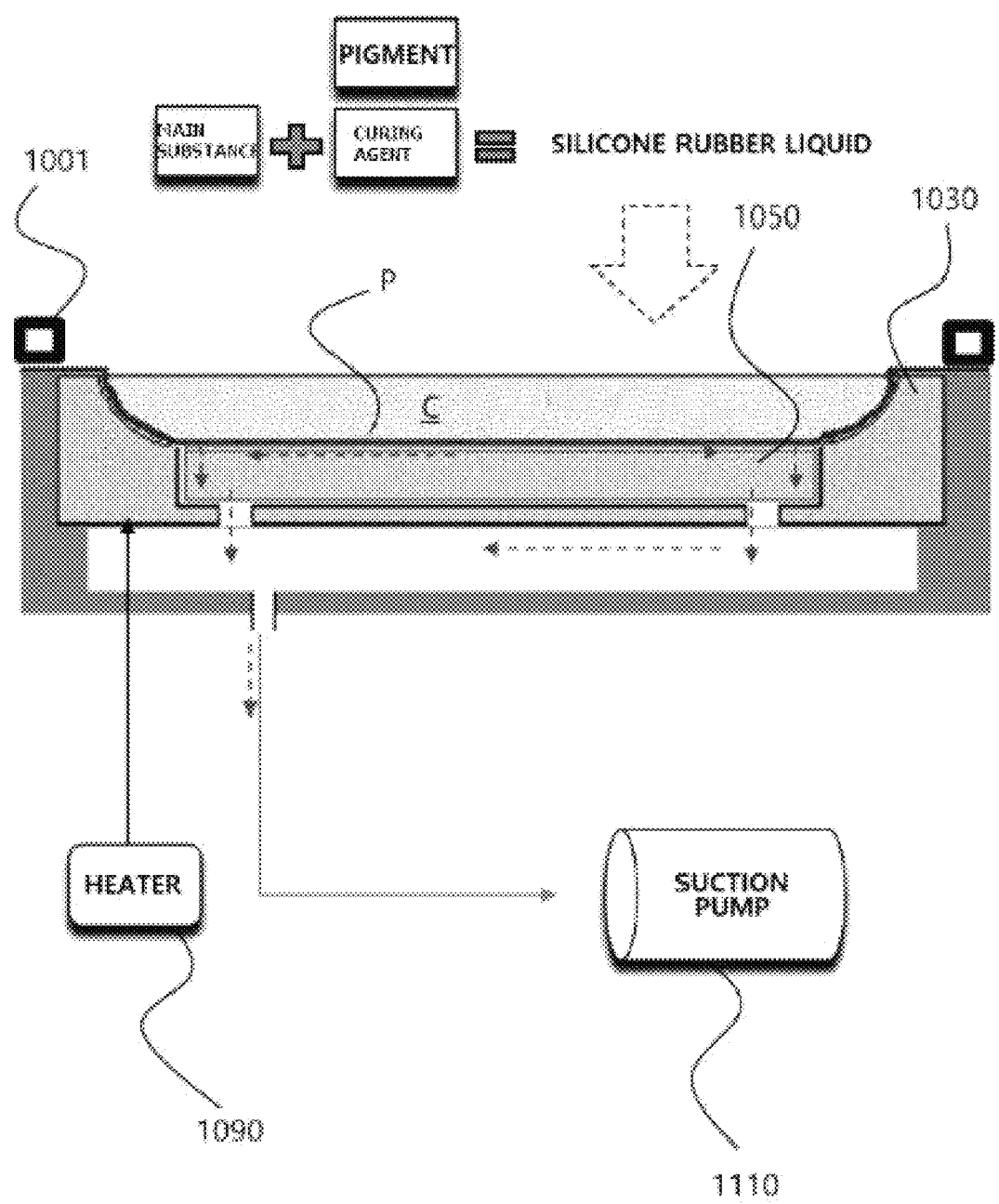

A liquid silicone rubber input step 1205 is a step of introducing the liquid silicone rubber component over the outer film P in the mold-film double layer emboss structure. This step is shown in more detail in FIG. 15. Referring to FIG. 15, a step 1205 of introducing a liquid silicone rubber among the method 1200 for manufacturing an elastic microcell surface structure according to the present disclosure is illustrated.

The liquid silicone rubber composition introduced in the illustrated step may use the materials that has, after curing, for example, a shore hardness of about 10 to 45, which may be the same as or softer than that of a normal human skin. This may be, for example, a liquid silicone rubber composition prepared by mixing a main substance and a curing agent, optionally mixing other additives such as pigments or oils, and then removing air bubbles. Pure liquid silicone rubber may be transparent when cured. Therefore, a small amount of at least a color pigment component may be added to realize various color products. Since the oil component tends to increase the adhesive strength with the outer film because the surface of the cured silicone rubber becomes sticky, it can be added in small amounts by adjusting the content empirically.

Two-component room temperature curing silicone rubbers are well known in the art. It may be cured if left unchanged at room temperature in a state in which a curing agent may be mixed with the main substance. In addition, silicone rubber tends to cure faster when the temperature may be higher than room temperature. According to the manufacturing method according to the present disclosure, in the process of curing the silicone rubber, it is sufficient if the mold member is heated to a temperature such that severe deformation such as melting of the outer film does not occur. Therefore, the mold member may be heated to about 70~150° C. depending on the exemplary embodiment. However, even in the case of a high temperature such that the outer film does not melt, yellowing may sometimes occur in the cured silicone rubber. This yellowing phenomenon may be not a problem when manufacturing a product having color. Once the silicone rubber is cured to a certain shape of an elastomer body, unlike the thermoplastic elastic resin material used as an outer shell, it has a characteristic that it cannot deform the shape by applying heat.

In the previous step, the outer film P was in close contact with the surfaces of the recesses and protrusions of the cavity C of the mold member, that is, the surface of the emboss pattern, thereby forming a mold-film double layer emboss structure. Therefore, the liquid silicone rubber introduced into the cavity C may be formed in a shape corresponding to the shape of the cavity C, in particular, a uneven structure corresponding to the mold-film double-layer emboss structure on the bottom surface of the cavity C may be formed.

Figure 16:
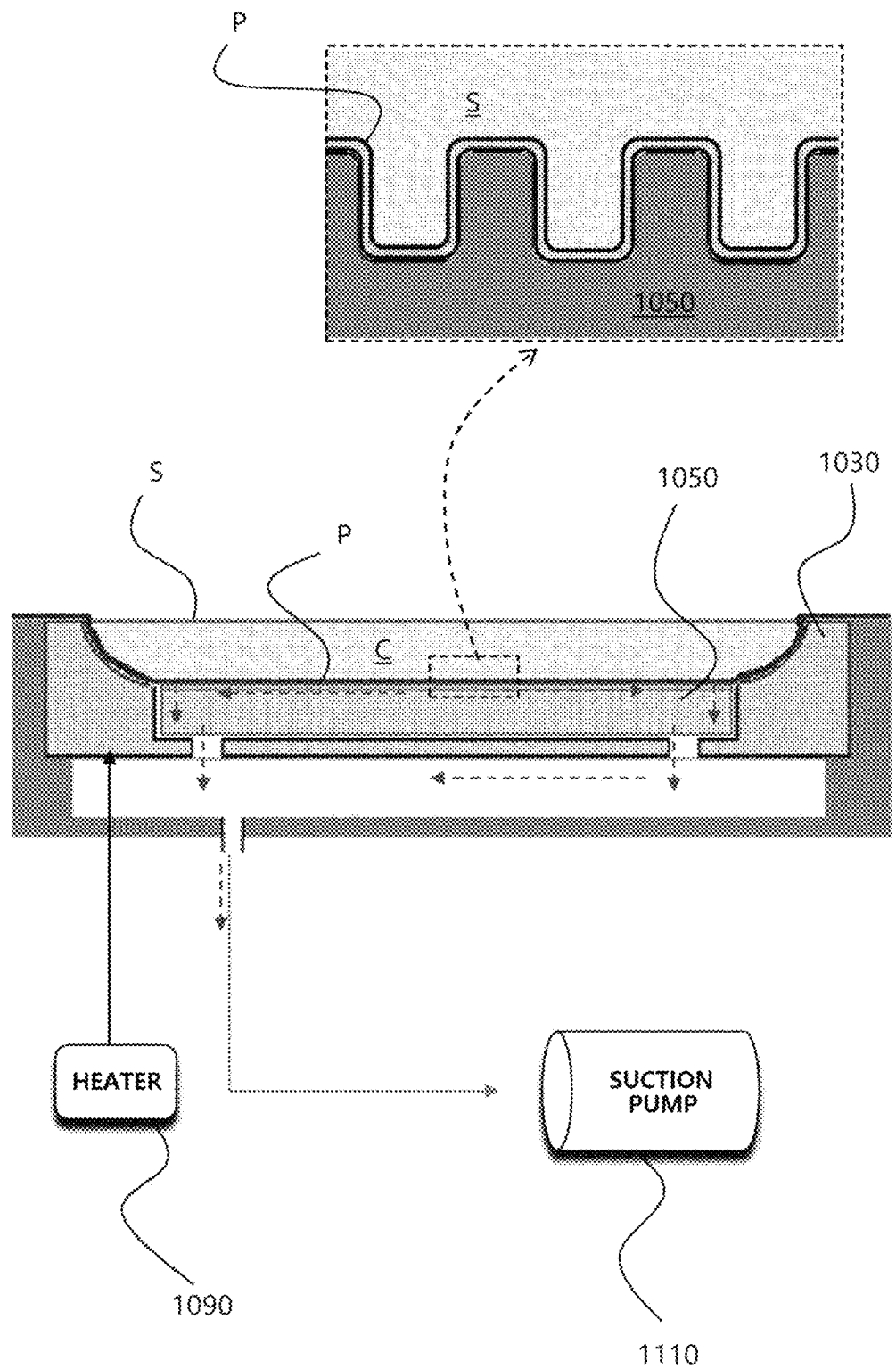

In the curing step 1207, the silicone rubber liquid introduced into the cavity C is cured to become an elastomer body S for an elastic microcell surface structure, and at the same time, the outer film P may be strongly adhered or attached to the outer surface of the elastomer body S. This step is shown in more detail in FIG. 16. Referring to FIG. 16, a curing step 1207 is illustrated in a method 1200 for manufacturing an elastic microcell surface structure according to the present disclosure.

The illustrated steps maintain the state of suction by the suction pump and heating by the heater. This state is maintained until the silicone rubber liquid is cured to an elastomer body S, for example, for 1 to 5 minutes. As a result, the outer surface of the thin elastic resin material P may be in close contact with the surface of the silicone rubber elastomer body S, thereby producing an elastic microcell surface structure disk.

The manufactured disc may be applied to a subsequent finishing process by covering the cover film V or separating it from the mold as it is.

And referring again to FIG. 12, the finishing steps 1209, 1211, and 1213 are processes of finishing the applicator semi-finished products (for example, see the sample picture in FIG. 8) manufactured in the previous step to form a product. Depending on the type of product, three finishing processes are possible.

First, the first finishing step 1209 is a process of making a product into a product to be put on a finger. That is, the ribbon strip may be disposed on the cover film V of the semi-finished product separated in FIG. 17. Then, along the rim, the outer film P, the cover film V and the ribbon strip are heat-sealed and cut. Accordingly, it is possible to complete the product of the silicone puff 30 of the type illustrated in FIG. 3. In an exemplary embodiment, the outer film P, the cover film V, and the ribbon strip are all made of a thermoplastic resin (for example, thermoplastic polyurethane) material, and heat bonding and cutting operations may be performed using a high frequency heat adhesive.

Figure 17:
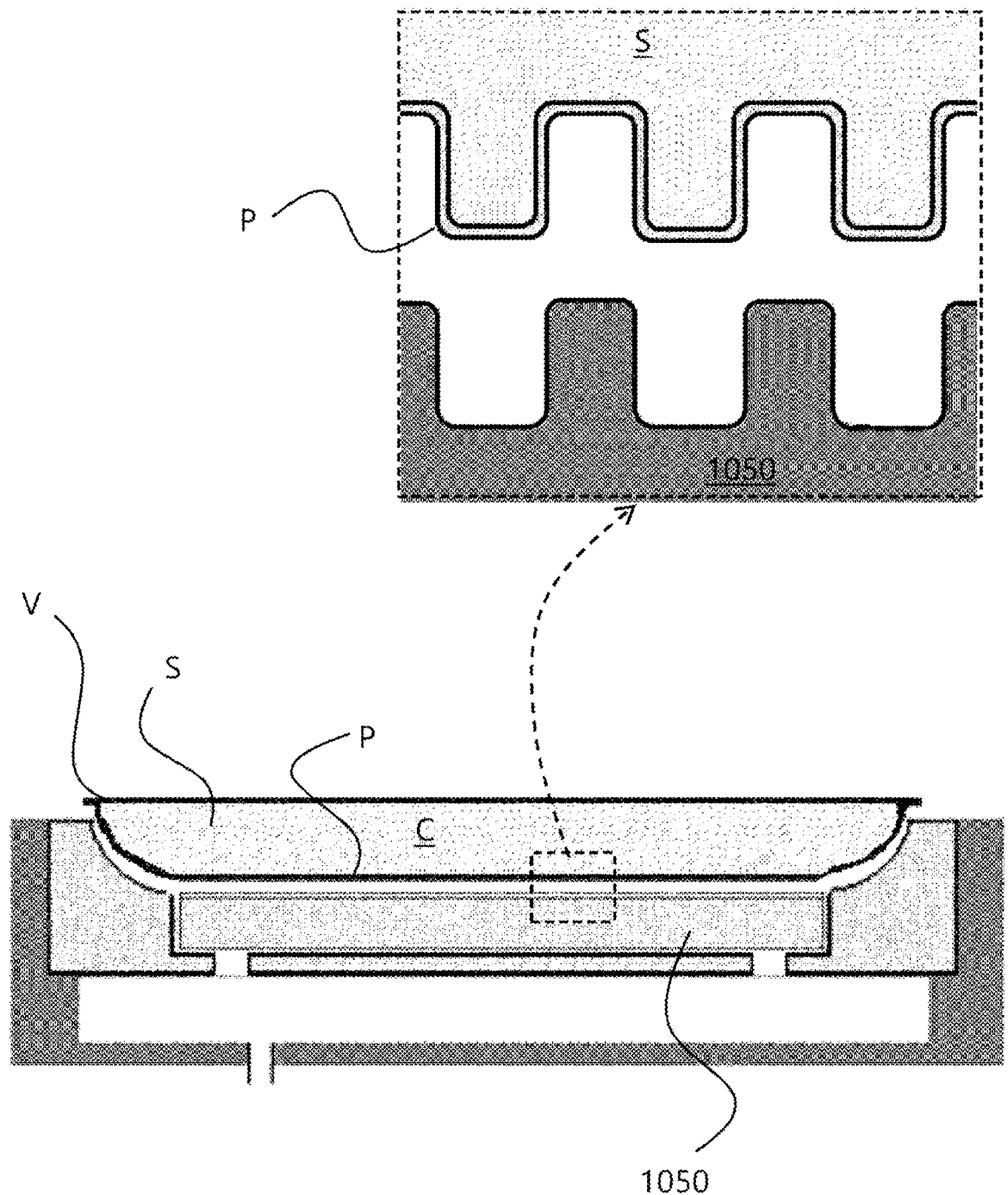
Figure 18:
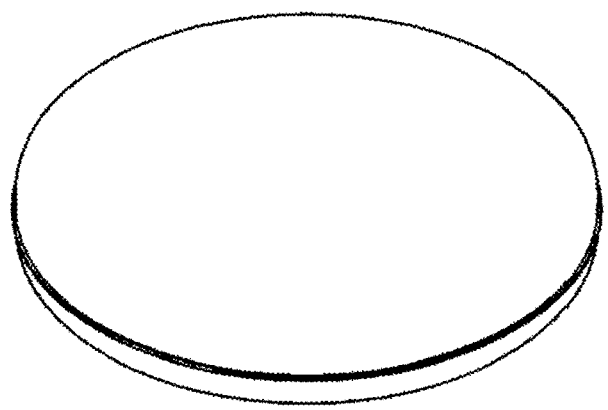
FIG. 18 is a schematic view showing another example of a product having an elastic microcell surface structure according to an exemplary embodiment of the present disclosure.
Figure 19:
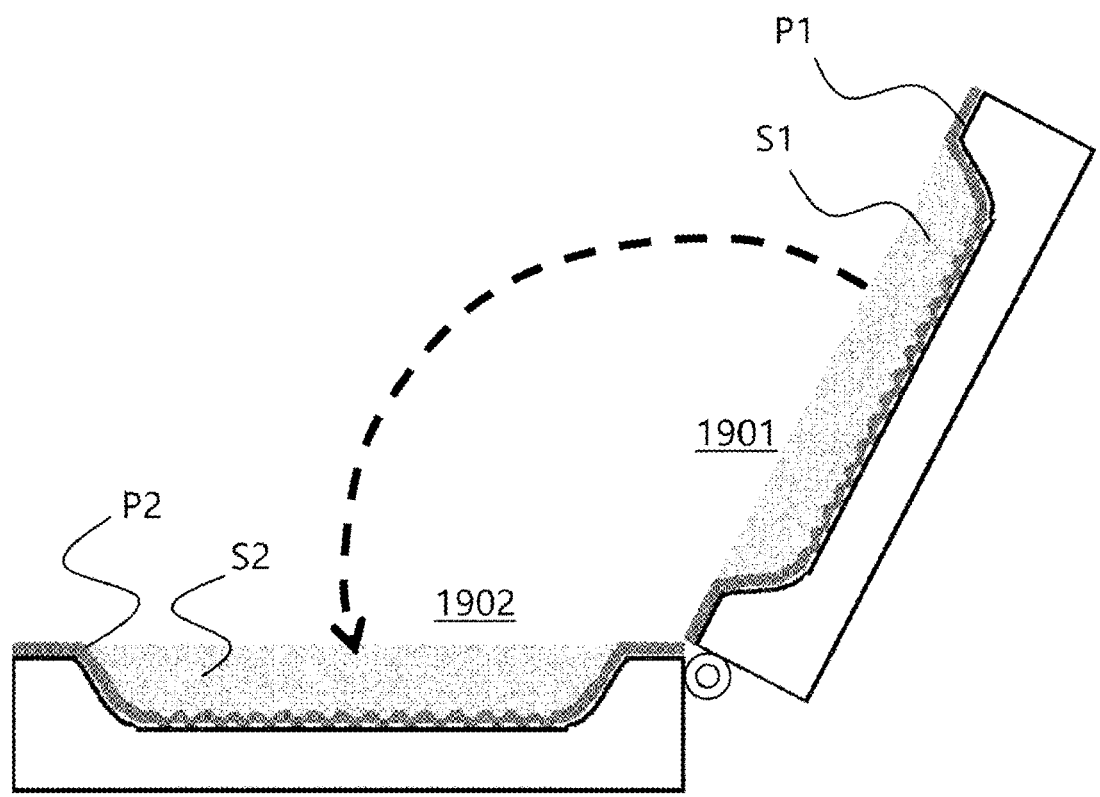
FIGS. 19 and 20 are schematic views for explaining the process of manufacturing the exemplary embodiment shown in FIG. 18.
Figure 20:
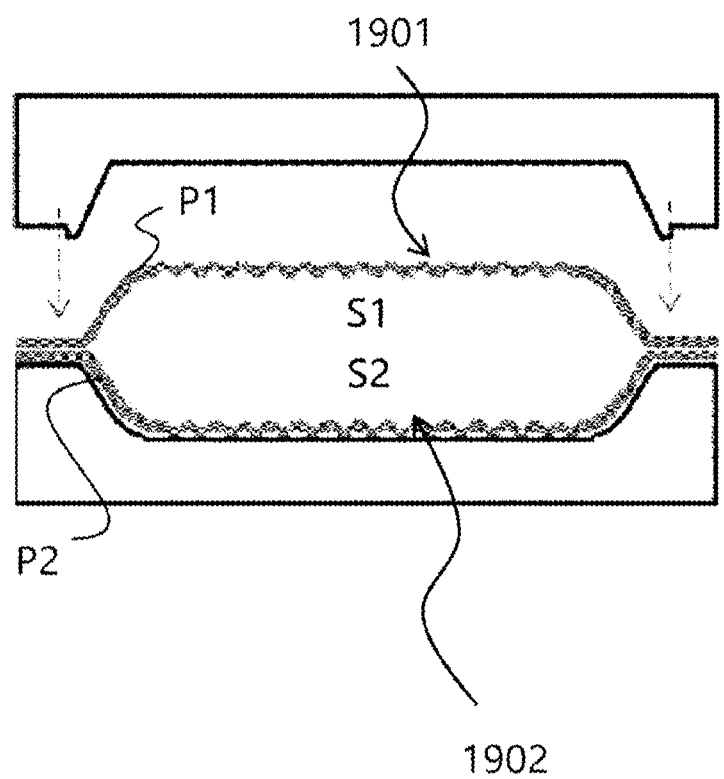

On the other hand, the second finishing step 1211 in FIG. 12 is a step of manufacturing a product of a type having dispensing surfaces on both sides by combining the pair of discs manufactured in the step of FIG. 17. This may have a shape in which two discs are overlapped as illustrated in FIG. 18. The manufacturing process of this type product is shown in more detail in FIGS. 19 and 20. FIGS. 19 and 20 are schematic diagrams for explaining a process of manufacturing the exemplary embodiment illustrated in FIG. 18.

Referring to FIG. 19, a process of overlapping a pair of discs 1901 and 1902 in which the upper surfaces of the elastic bodies S1 and S2 are exposed without the cover film so that the upper surfaces come into contact with each other is illustrated. Then, as shown in FIG. 20, in the overlapped state, the outer films P1 and P2 of the pair of discs 1901 and 1902 along the edge of the elastic bodies S1 and S2, for example, using a high-frequency thermal adhesive, by heat-sealing and cutting, a silicone puff product having dispensing surfaces on each side can be produced.

In this case, it is possible that any one of the two dispensing surfaces may have no emboss pattern. It is also possible to have an example in which the emboss patterns of both coated surfaces have different types of patterns. This product has the advantage that emboss is formed on both sides, instead of having a separate gripping part.

Figure 21:
FIG. 21 is a schematic diagram showing another example of a product having an elastic microcell surface structure according to an exemplary embodiment of the present disclosure.
Figure 22:
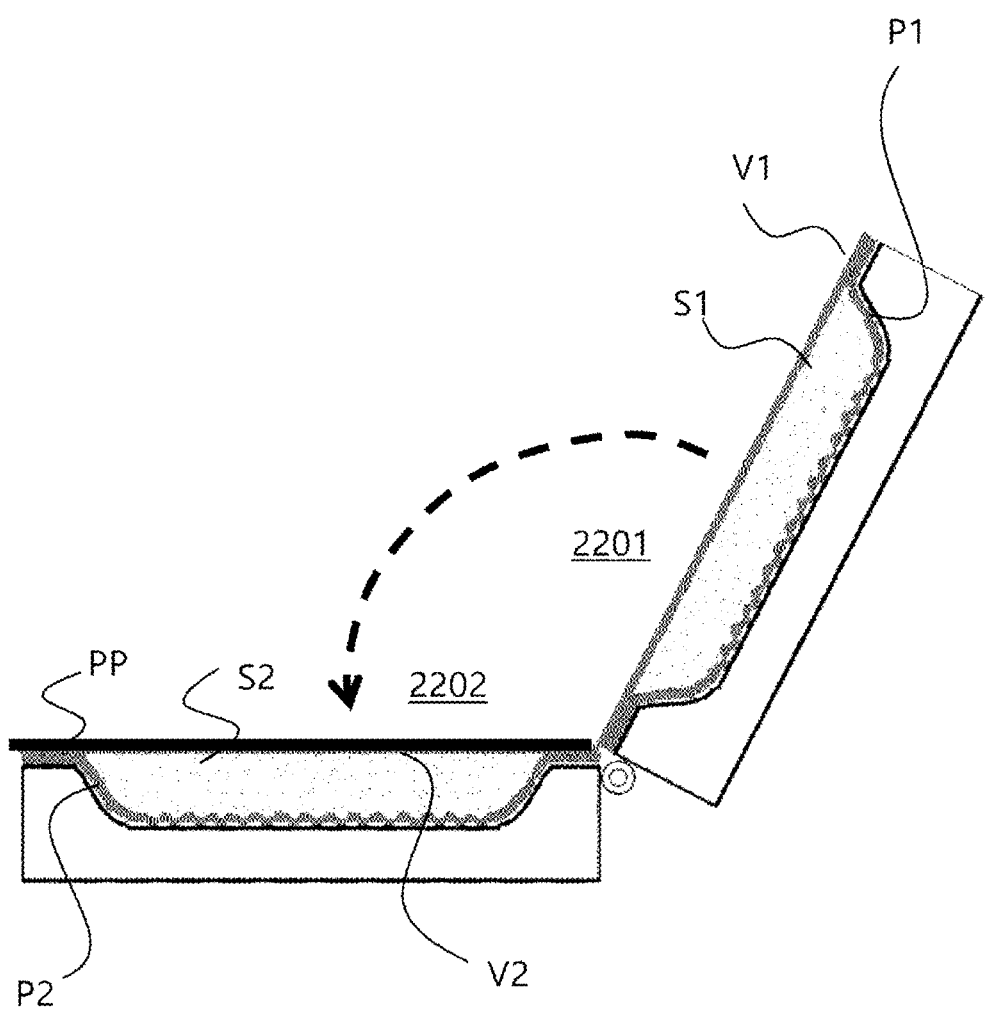
FIGS. 22 and 23 are schematic diagrams for explaining the process of manufacturing the exemplary embodiment shown in FIG. 21.
Figure 23:
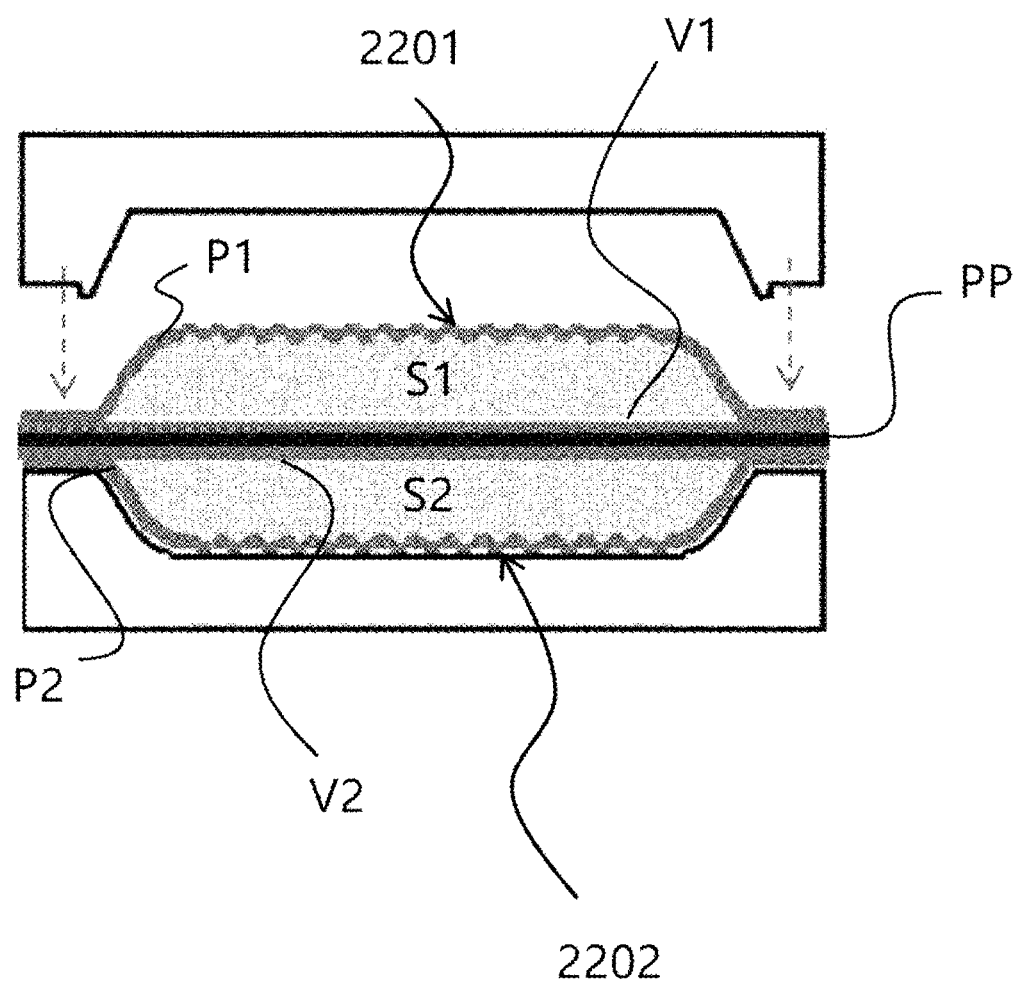

In addition, the third finishing step 1213 in FIG. 12 is a step of manufacturing a product in which a pair of discs manufactured in FIG. 17 are combined so that fingers can be fitted while having a coating surface on each side. This is a product of a type that can fit a finger in the middle in the shape of two disks overlapped as shown in FIG. 21. The manufacturing process of this product is shown in more detail in FIGS. 22 and 23. FIGS. 22 and 23 are schematic diagrams for describing a process of manufacturing the exemplary embodiment shown in FIG. 21.

Referring to FIG. 22, a pair of disks 2201 and 2202, each of which covers the upper surfaces of the elastic bodies S1 and S2 with the cover films V1 and V2, may be protected between the two cover films V1 and V2. The process of overlapping the two cover films V1 and V2 in contact with each other in the state in which the protective film PP may be fitted as illustrated.

The protective film PP may be, for example, polyethylene, polypropylene or other material, a material having a higher glass transition temperature than the polyurethane film is sufficient. The protective film PP may be, for example, not in a circular shape but in a long and narrow strip form, and may be disposed in such a way that only a partial area may be covered, rather than all the borders between the pair of discs 2201 and 2202.

Then, as shown in FIG. 23, in the overlapped state, the outer films P1 and P2, the cover films V1 and V2 and the protective film PP of the pair of disks 2201 and 2202 are heat-sealed and cut along a rim of elastic bodies S1 and S2, for example, using a high-frequency heat sealer. Then, both the outer films P1 and P2 and the cover films V1 and V2 are fused and cut by the temperature of the high-frequency heat-sealing machine at the edge of the portion where the protective film PP may be not covered. On the other hand, the outer film P1 and the cover film V1 of the first disk 2201 are fused to each other and cut at the rim of the portion covered with the protective film PP, and the outer film P2 of the second disk 2202 and the cover film V2 are fused to each other and cut.

As a result, a product having dispensing surfaces on both sides and a portion covered with the protective film PP can be manufactured to be able to insert a finger between the two disks 2201 and 2202. In this case, similar to the product made in the second finishing step 1211, any one of the two coated surfaces may be an example without an emboss pattern, and an example in which the emboss patterns of both coated surfaces may have different types of patterns is also possible.

Figure 24:
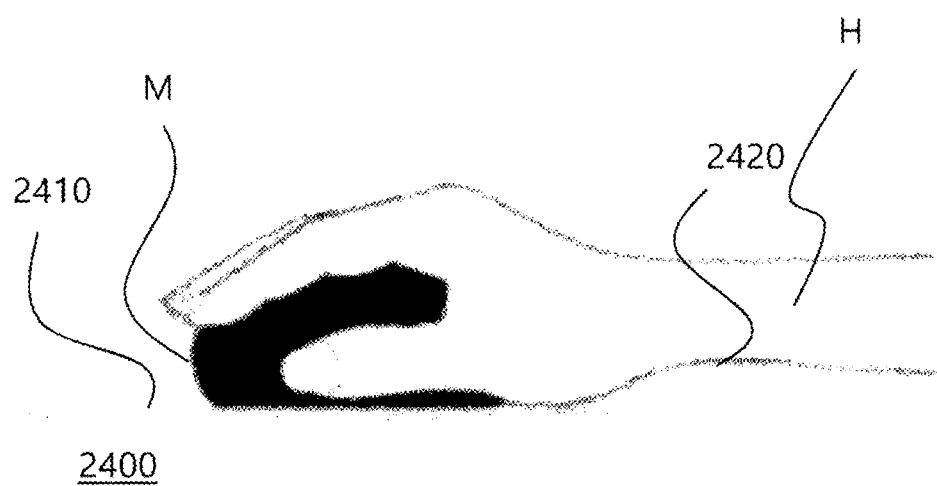
FIG. 24 is a schematic view illustrating a mouse pad in which a microcell surface structure according to an exemplary embodiment of the present disclosure is applied as a mouse contact surface and a wrist contact surface.

FIG. 24 is a schematic diagram illustrating a mouse pad to which a microcell surface structure that can be provided according to an exemplary embodiment of the present disclosure may be applied as a mouse contact surface and a wrist contact surface.

Referring to FIG. 24, the illustrated mouse pad 2400 includes a mouse contact surface 2410 and a wrist protector 2420. The bottom surface of the mouse M contacts the mouse contact surface 2410 and slides as the user holds the mouse M in hand and moves it.

The surface of the existing mouse contact surface or the wrist protector may be made of an elastic resin material, or may be coated with a textile material. In the case of a mouse contact surface made of an elastic resin material, there may be a problem that the surface of the resin material and the bottom surface of the mouse stick to each other, so that it does not slip well. Even when the wrist protector has a resin material surface, it has the disadvantage that it feels poor because it adheres to the skin. On the other hand, when the outer shell of the fabric material was coated, the phenomenon of sticking was removed, but when dust or foreign substances adhered, it was difficult to remove it, and there was a disadvantage in that it was not good for hygiene.

On the other hand, when the elastic microcell surface structure according to the present disclosure is applied to the mouse contact surface 2410 and/or the wrist protector 2420 of the mouse pad 2400, not only can the phenomenon that the mouse M or the wrist H adheres to the surface be removed, thus providing a product with improved tactile feeling, but also cleaning of dust or foreign substances may be facilitated, thus providing a hygienic advantage.

In the above, the present disclosure has been described through specific exemplary embodiments, but those skilled in the art can make various modified products by applying and exemplifying the elastic microcell surface structure as an dispensing surface or surface by referring to and combining various features described in this specification. Therefore, it may be pointed out that the scope of the present disclosure is not limited to the described exemplary embodiments, but should be interpreted by the appended claims.

What is claimed is:

1. An elastic microcell surface structure for an elastomer body with an outer film adhered,
   wherein the elastomer body comprises a solid uneven structure formed of protruding portions and recess portions formed at a surface thereof, and
   wherein the outer film includes a zigzag uneven structure being closely wrapped around the protruding portions and recess portions of the solid uneven structure of the elastomer body.

2. The elastic microcell surface structure of claim 1, wherein in the solid uneven structure of the elastomer body, the protruding portions are connected to each other in a horizontal direction in the form of a net, and the recess portions includes a plurality of recesses wherein each of the recesses is isolated by the protruding portion.

3. The elastic microcell surface structure of claim 1, wherein s thickness of the outer film is 0.01~0.10 mm, and s depth of the recess portions is 2 to 20 times the thickness of the outer film.

4. The elastic microcell surface structure of claim 1, wherein the elastomer body comprises any one of silicone rubber and urethane rubber.

5. The elastic microcell surface structure of claim 1, wherein the outer film comprises a thermoplastic polyurethane film.

6. A cosmetic applicator comprising a dispensing surface which comprises the elastic microcell surface structure as claimed in claim 1.

7. A mouse pad comprising a contact surface being contacted with a mouse or a user wrist, wherein the contact surface comprises the elastic microcell surface structure as claimed in claim 1.

8. A method of manufacturing an elastic microcell surface structure for an elastomer body with an outer film adhered, comprising the steps of:
   preparing a mold cavity having an emboss pattern of solid uneven structure having recess portions and protruding portions;
   disposing an outer film over the surface of the emboss pattern of the mold cavity;
   removing air between the emboss pattern of the mold cavity and the outer film so that the outer film closely contacts the surfaces of the recess portions and the protruding portions of the emboss pattern to form a zigzag uneven structure;
   introducing a liquid elastomer composition into the mold-film double layer emboss structure formed by contacting the outer film with the surface of the emboss pattern of the mold cavity; and
   curing the liquid elastomer composition.

9. The method of claim 8, wherein:
   the recess portions of the emboss pattern are a plurality of recesses that is formed by connecting the recess portions laterally in the form of a mesh,
   the protruding portions of the emboss pattern include a plurality of protrusions separated by the recesses, and
   the air between the outer film and the emboss pattern is sucked through the recess portions connected to each other in the form of the net.

10. The method of claim 8, wherein a thickness of the outer film is 0.01~0.10 mm, and a depth of the recess portions is 2 to 20 times the thickness of the outer film.

11. The method of claim 8, after the curing the liquid elastomer composition, further comprising the steps of:
   separating a semi-finished product from the mold cavity, wherein the semi-finished product has the elastomer body being cured and the outer film adhered thereon; and
   arranging a cover film and a ribbon strip on the separated semi-finished product; and
   thermally bonding and cutting the outer film, the cover film and the ribbon strip along the edge of the semi-finished product.

12. The method of claim 8, after the curing the liquid elastomer composition, further comprising the steps of:
   separating a pair of semi-finished product from the mold cavity, wherein each of the semi-finished products has the elastomer body being cured and the outer film adhered thereon;
   overlapping the pair of separated semi-finished products such that top surfaces of the elastomer bodies are in contact with each other; and
   thermally bonding and cutting the outer films of the pair of the semi-finished products along the edge of the semi-finished product.

13. The method of claim 8, after the curing the liquid elastomer composition, further comprising the steps of:
   separating a semi-finished product from the mold cavity, wherein the semi-finished product has the elastomer body being cured and the outer film adhered thereon;
   covering a cover film on top of the separated pair of semi-elastomer body, respectively;
   overlapping the pair of semi-finished products covered with the cover film such that the two cover films are in contact with each other;
   arranging a protective film between two overlapping cover films to cover only a part of an edge of the semi-finished product; and
   thermally bonding and cutting the outer film and the cover film along the edge of the semi-finished product.

14. An apparatus for manufacturing an elastic microcell surface structure including an outer film adhered to an elastomer body, the apparatus comprising:
   a mold cavity with an emboss pattern including recess portions and protruding portions;
   a heater for heating the mold cavity to a predetermined temperature;
   a pressing member for sealing a space between the emboss pattern of the mold cavity and an outer film disposed thereon by pressing an edge of the outer film along an edge of the mold cavity;
   a suction pump for sucking and removing air from the space between the emboss pattern and the outer film.

15. The apparatus of claim 14, wherein at the mold cavity the recess portions of the emboss pattern are connected laterally to each other in the form of a net, and wherein the protruding portions of the emboss pattern include a plurality of protrusions separated by the recess portions.

16. The apparatus of claim 14, wherein a thickness of the outer film is 0.01~0.10 mm, and the depth of the recess portions is 2 to 20 times the thickness of the outer film.

17. The apparatus of claim 14, wherein the emboss pattern is formed by a separately manufactured pattern member, and the pattern member is assembled inside the mold cavity.

18. The apparatus of claim 17, wherein the emboss patterns are formed on either or both surfaces of the pattern member.

* * * * *